(12) United States Patent
Meadows et al.

(10) Patent No.: US 9,849,288 B2
(45) Date of Patent: *Dec. 26, 2017

(54) APPARATUS, SYSTEM, AND METHOD FOR SELECTIVE STIMULATION

(71) Applicant: ImThera Medical, Inc., San Diego, CA (US)

(72) Inventors: Paul M. Meadows, Glendale, CA (US); Marcelo G. Lima, San Diego, CA (US); Stanley R. Craig, Westport, MA (US)

(73) Assignee: IMTHERA MEDICAL, INC., San Diego, CA (US)

( * ) Notice: Subject to any disclaimer, the term of this patent is extended or adjusted under 35 U.S.C. 154(b) by 46 days.

This patent is subject to a terminal disclaimer.

(21) Appl. No.: 13/775,349

(22) Filed: Feb. 25, 2013

(65) Prior Publication Data

US 2013/0165996 A1    Jun. 27, 2013

Related U.S. Application Data

(63) Continuation of application No. 12/681,812, filed as application No. PCT/US2008/011598 on Oct. 9, 2008, now abandoned.

(60) Provisional application No. 61/136,102, filed on Aug. 12, 2008, provisional application No. 61/017,614, filed on Dec. 29, 2007, provisional application No. 60/978,519, filed on Oct. 9, 2007.

(51) Int. Cl.
| | |
|---|---|
| A61N 1/05 | (2006.01) |
| A61N 1/36 | (2006.01) |
| A61N 1/375 | (2006.01) |
| A61N 1/378 | (2006.01) |

(52) U.S. Cl.
CPC .......... *A61N 1/3611* (2013.01); *A61N 1/0556* (2013.01); *A61N 1/3605* (2013.01); *A61N 1/375* (2013.01); *A61N 1/378* (2013.01); *A61N 1/36071* (2013.01); *A61N 1/36135* (2013.01); *A61N 1/3758* (2013.01)

(58) Field of Classification Search
CPC .................................................... A61N 1/0556
USPC .............................................. 607/36, 42, 118
See application file for complete search history.

(56) References Cited

U.S. PATENT DOCUMENTS

| | | |
|---|---|---|
| 4,424,812 A | 1/1984 | Lesnick |
| 4,602,624 A | 7/1986 | Naples et al. |

(Continued)

FOREIGN PATENT DOCUMENTS

| | | |
|---|---|---|
| EP | 1524007 | 4/2005 |
| EP | 2116274 A2 | 11/2009 |

(Continued)

OTHER PUBLICATIONS

Final Office Action dated Feb. 9, 2012 in connection with U.S. Appl. No. 13/097,172.

(Continued)

*Primary Examiner* — Eric D. Bertram
(74) *Attorney, Agent, or Firm* — Morgan, Lewis & Bockius LLP

(57) ABSTRACT

An implantable neurostimulator system is disclosed, the neurostimulator system comprising a hollow cylindrical electronics enclosure having a top, a bottom, and a side; a coil extending from a first part of the electronics enclosure; and at least one electrode operatively connected to the electronics enclosure.

18 Claims, 29 Drawing Sheets

(56) References Cited

U.S. PATENT DOCUMENTS

| | | |
|---|---|---|
| 5,094,242 A | 3/1992 | Gleason et al. |
| 5,095,905 A | 3/1992 | Klepinski |
| 5,123,425 A | 6/1992 | Shaonnon, Jr. et al. |
| 5,133,354 A | 7/1992 | Kallok |
| 5,146,918 A | 9/1992 | Kallok et al. |
| 5,158,080 A | 10/1992 | Kallok |
| 5,174,287 A | 12/1992 | Kallok et al. |
| 5,190,053 A | 3/1993 | Meer |
| 5,211,173 A | 5/1993 | Kallok et al. |
| 5,215,082 A | 6/1993 | Kallok et al. |
| 5,233,983 A | 8/1993 | Markowitz |
| 5,281,219 A | 1/1994 | Kallok |
| 5,300,094 A | 4/1994 | Kallok et al. |
| 5,344,438 A | 9/1994 | Testerman et al. |
| 5,483,969 A | 1/1996 | Testerman et al. |
| 5,522,862 A | 6/1996 | Testerman et al. |
| 5,540,731 A | 7/1996 | Testerman |
| 5,540,732 A | 7/1996 | Testerman |
| 5,540,733 A | 7/1996 | Testerman et al. |
| 5,545,201 A | 8/1996 | Helland et al. |
| 5,546,952 A | 8/1996 | Erickson |
| 5,591,216 A | 1/1997 | Testerman et al. |
| 5,634,462 A * | 6/1997 | Tyler et al. .................. 600/377 |
| 5,713,922 A | 2/1998 | King |
| 5,771,891 A | 6/1998 | Gozani |
| 5,837,006 A | 11/1998 | Ocel et al. |
| 5,871,512 A | 2/1999 | Hemming et al. |
| 5,988,171 A | 11/1999 | Sohn et al. |
| 6,021,352 A | 2/2000 | Christopherson et al. |
| 6,051,017 A | 4/2000 | Loeb et al. |
| 6,132,384 A | 10/2000 | Christopherson et al. |
| 6,175,767 B1 | 1/2001 | Doyle, Sr. |
| 6,212,435 B1 | 4/2001 | Lattner et al. |
| 6,240,316 B1 | 5/2001 | Richmond et al. |
| 6,251,126 B1 | 6/2001 | Ottenhoff et al. |
| 6,266,560 B1 | 7/2001 | Zhang et al. |
| 6,269,269 B1 | 7/2001 | Ottenhoff et al. |
| 6,345,202 B2 | 2/2002 | Richmond et al. |
| 6,408,852 B2 | 6/2002 | Tielemans |
| 6,409,676 B2 | 6/2002 | Ruton et al. |
| 6,415,174 B1 | 7/2002 | Bebehani et al. |
| 6,427,689 B1 | 8/2002 | Estes et al. |
| 6,432,956 B1 | 8/2002 | Dement et al. |
| 6,454,724 B1 | 9/2002 | Greene |
| 6,456,866 B1 | 9/2002 | Tyler et al. |
| 6,475,156 B1 | 11/2002 | Vega |
| 6,488,634 B1 | 12/2002 | Rapoport et al. |
| 6,516,802 B2 | 2/2003 | Hansen et al. |
| 6,516,805 B1 | 2/2003 | Thornton |
| 6,529,752 B2 | 3/2003 | Krausman et al. |
| 6,536,439 B1 | 3/2003 | Palmisano |
| 6,555,564 B1 | 4/2003 | Radulovacki et al. |
| 6,572,543 B1 | 6/2003 | Christopherson et al. |
| 6,574,507 B1 | 6/2003 | Bonnet |
| 6,580,944 B1 | 6/2003 | Katz et al. |
| 6,586,478 B2 | 7/2003 | Ackman et al. |
| 6,587,725 B1 | 7/2003 | Durand et al. |
| 6,594,370 B1 | 7/2003 | Anderson |
| 6,595,215 B2 | 7/2003 | Wood |
| 6,613,779 B2 | 9/2003 | Mondadori et al. |
| 6,629,527 B1 | 10/2003 | Estes et al. |
| 6,635,021 B1 | 10/2003 | Sullivan et al. |
| 6,636,767 B1 | 10/2003 | Knudson et al. |
| 6,641,542 B2 | 11/2003 | Cho et al. |
| 6,658,301 B2 | 12/2003 | Loeb et al. |
| 6,666,830 B1 | 12/2003 | Lehrman et al. |
| 6,671,907 B1 | 1/2004 | Zuberi |
| 6,705,315 B2 | 3/2004 | Sullivan et al. |
| 6,727,242 B2 | 4/2004 | Rudulovack et al. |
| 6,729,335 B1 | 5/2004 | Halstrom |
| 6,731,984 B2 | 5/2004 | Cho et al. |
| 6,752,766 B2 | 6/2004 | Kowallik et al. |
| 6,761,167 B1 | 7/2004 | Nadjafizadeh et al. |
| 6,761,168 B1 | 7/2004 | Nadjafizadeh et al. |
| 6,766,802 B1 | 7/2004 | Keropian |
| 6,770,022 B2 | 8/2004 | Mechlenburg et al. |
| 6,770,037 B2 | 8/2004 | Sullivan et al. |
| 6,773,404 B2 | 8/2004 | Poezevera et al. |
| 6,776,162 B2 | 8/2004 | Wood |
| 6,788,975 B1 | 9/2004 | Whitehurst et al. |
| 6,793,629 B2 | 9/2004 | Rapoport et al. |
| 6,807,967 B2 | 10/2004 | Wood |
| 6,811,538 B2 | 11/2004 | Westbrook et al. |
| 6,814,074 B1 | 11/2004 | Nadjafizadeh et al. |
| 6,818,665 B2 | 11/2004 | Wennerholm et al. |
| 6,835,740 B2 | 12/2004 | Rubin et al. |
| 6,878,121 B2 | 4/2005 | Krausman et al. |
| 6,881,192 B1 | 4/2005 | Park |
| 6,884,596 B2 | 4/2005 | Civelli et al. |
| 6,857,149 B2 | 5/2005 | Hoggatt et al. |
| 6,890,306 B2 | 5/2005 | Poezevera |
| 6,893,405 B2 | 5/2005 | Kumar et al. |
| 6,901,292 B2 | 5/2005 | Hrdlicka et al. |
| 6,904,320 B2 | 6/2005 | Park et al. |
| 6,918,394 B2 | 7/2005 | Matsuda et al. |
| 6,928,324 B2 | 8/2005 | Park et al. |
| 6,964,641 B2 | 11/2005 | Cho et al. |
| 6,999,819 B2 | 2/2006 | Swoyer et al. |
| 7,003,352 B1 | 2/2006 | Whitehurst |
| 7,092,763 B1 | 8/2006 | Griffith et al. |
| 7,184,836 B1 | 2/2007 | Meadows et al. |
| 7,245,971 B2 | 7/2007 | Park et al. |
| 7,570,997 B2 | 8/2009 | Lovett et al. |
| 7,644,714 B2 | 1/2010 | Atkinson et al. |
| 7,680,538 B2 | 3/2010 | Durand et al. |
| 7,725,195 B2 | 5/2010 | Lima et al. |
| 7,809,442 B2 | 10/2010 | Bolea et al. |
| 2001/0000346 A1 | 4/2001 | Ruton et al. |
| 2001/0001125 A1 | 5/2001 | Schulman et al. |
| 2001/0010010 A1 | 7/2001 | Richmond et al. |
| 2001/0015204 A1 | 8/2001 | Hansen et al. |
| 2001/0018557 A1 | 8/2001 | Lynn et al. |
| 2001/0027793 A1 | 10/2001 | Tielemans |
| 2001/0041719 A1 | 11/2001 | Mondadori et al. |
| 2001/0046988 A1 | 11/2001 | Iglehart |
| 2002/0007127 A1 | 1/2002 | Sullivan et al. |
| 2002/0015740 A1 | 2/2002 | Ackman et al. |
| 2002/0019669 A1 * | 2/2002 | Berrang ............ A61N 1/36032 623/10 |
| 2002/0037533 A1 | 3/2002 | Civelli et al. |
| 2002/0049479 A1 | 4/2002 | Pitts |
| 2002/0059935 A1 | 5/2002 | Wood |
| 2002/0086870 A1 | 7/2002 | Radulovacki et al. |
| 2002/0092527 A1 | 7/2002 | Wood |
| 2002/0095076 A1 | 7/2002 | Krausman et al. |
| 2002/0099033 A1 | 7/2002 | Meyer et al. |
| 2002/0100477 A1 | 8/2002 | Sullivan et al. |
| 2002/0124848 A1 | 9/2002 | Sullivan et al. |
| 2002/0124849 A1 | 9/2002 | Billette De Villemeur et al. |
| 2002/0144684 A1 | 10/2002 | Moone |
| 2002/0144685 A1 | 10/2002 | Ivanovich et al. |
| 2002/0165246 A1 | 11/2002 | Holman |
| 2002/0165462 A1 | 11/2002 | Wesbrook et al. |
| 2002/0169384 A1 | 11/2002 | Kowallik et al. |
| 2002/0173707 A1 | 11/2002 | Lynn et al. |
| 2002/0175821 A1 | 11/2002 | Ruppel |
| 2002/0183306 A1 | 12/2002 | Howard, Jr. |
| 2002/0193697 A1 | 12/2002 | Cho et al. |
| 2002/0193839 A1 | 12/2002 | Cho et al. |
| 2003/0004423 A1 | 1/2003 | Lavie et al. |
| 2003/0015198 A1 | 1/2003 | Heeke et al. |
| 2003/0021772 A1 | 1/2003 | Birkmayer |
| 2003/0053956 A1 | 3/2003 | Hofmann |
| 2003/0055346 A1 | 3/2003 | Rapoport et al. |
| 2003/0055348 A1 | 3/2003 | Chazal et al. |
| 2003/0056785 A1 | 3/2003 | Narihiko et al. |
| 2003/0083241 A1 | 5/2003 | Young |
| 2003/0093131 A1 | 5/2003 | Loeb et al. |
| 2003/0130266 A1 | 7/2003 | Radulovacki et al. |
| 2003/0130589 A1 | 7/2003 | Poezevera |
| 2003/0139680 A1 | 7/2003 | Sheldon |
| 2003/0139691 A1 | 7/2003 | Kumar et al. |
| 2003/0139789 A1 | 7/2003 | Tvinnereim et al. |
| 2003/0153953 A1 | 8/2003 | Park et al. |

(56) References Cited

U.S. PATENT DOCUMENTS

| | | |
|---|---|---|
| 2003/0153954 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0167018 A1 | 9/2003 | Wyckoff |
| 2003/0172462 A1 | 9/2003 | Hoggatt et al. |
| 2003/0176788 A1 | 9/2003 | Crutchfield et al. |
| 2003/0181958 A1 | 9/2003 | Dobak, III |
| 2003/0183227 A1 | 10/2003 | Klemperer |
| 2003/0195140 A1 | 10/2003 | Ackman et al. |
| 2003/0195571 A1 | 10/2003 | Burnes et al. |
| 2003/0204213 A1 | 10/2003 | Jensen et al. |
| 2003/0216789 A1 | 11/2003 | Deem et al. |
| 2003/0232839 A1 | 12/2003 | Hangauer et al. |
| 2003/0235313 A1 | 12/2003 | Kurzweil et al. |
| 2003/0236228 A1 | 12/2003 | Radulovacki et al. |
| 2004/0002516 A1 | 1/2004 | Mondadori et al. |
| 2004/0002742 A1 | 1/2004 | Florio |
| 2004/0006339 A1 | 1/2004 | Underwood et al. |
| 2004/0006375 A1 | 1/2004 | Poezevera |
| 2004/0016433 A1 | 1/2004 | Estes et al. |
| 2004/0020493 A1 | 2/2004 | Wood |
| 2004/0025885 A1 | 2/2004 | Payne, Jr. |
| 2004/0029869 A1 | 2/2004 | Iglehart, III |
| 2004/0030224 A1 | 2/2004 | Sotos et al. |
| 2004/0055597 A1 | 3/2004 | Virr et al. |
| 2004/0059240 A1 | 3/2004 | Cho et al. |
| 2004/0082519 A1 | 4/2004 | Hedner et al. |
| 2004/0087866 A1 | 5/2004 | Bowman et al. |
| 2004/0087878 A1 | 5/2004 | Krausman et al. |
| 2004/0097871 A1 | 5/2004 | Yerushalmy |
| 2004/0111041 A1 | 6/2004 | Ni et al. |
| 2004/0127572 A1 | 7/2004 | Carley et al. |
| 2004/0134491 A1 | 7/2004 | Pflueger et al. |
| 2004/0138719 A1 | 7/2004 | Cho et al. |
| 2004/0144391 A1 | 7/2004 | Brady et al. |
| 2004/0146873 A1 | 7/2004 | Ptacek et al. |
| 2004/0157813 A1 | 8/2004 | Wennerholm et al. |
| 2004/0172090 A1* | 9/2004 | Janzig ............... A61N 1/3605 607/45 |
| 2004/0176695 A1 | 9/2004 | Poezevara |
| 2004/0176809 A1 | 9/2004 | Cho et al. |
| 2004/0186523 A1 | 9/2004 | Florio |
| 2004/0187873 A1 | 9/2004 | Brown |
| 2004/0200472 A1 | 10/2004 | Gold |
| 2004/0210261 A1 | 10/2004 | King et al. |
| 2004/0215095 A1 | 10/2004 | Lee et al. |
| 2004/0225226 A1 | 11/2004 | Lehrman et al. |
| 2004/0235807 A1 | 11/2004 | Weinrich et al. |
| 2004/0254493 A1 | 12/2004 | Chervin et al. |
| 2005/0008587 A1 | 1/2005 | Schulz et al. |
| 2005/0015117 A1 | 1/2005 | Gerber |
| 2005/0016536 A1 | 1/2005 | Rapoport et al. |
| 2005/0020930 A1 | 1/2005 | Salisbury et al. |
| 2005/0022821 A1 | 2/2005 | Jeppesen |
| 2005/0027207 A1 | 2/2005 | Westbrook et al. |
| 2005/0031688 A1 | 2/2005 | Ayala |
| 2005/0034730 A1 | 2/2005 | Wood |
| 2005/0038013 A1 | 2/2005 | Gold |
| 2005/0039757 A1 | 2/2005 | Wood |
| 2005/0042589 A1 | 2/2005 | Hatlesstad et al. |
| 2005/0043645 A1 | 2/2005 | Ono et al. |
| 2005/0043652 A1 | 2/2005 | Lovett et al. |
| 2005/0045190 A1 | 3/2005 | Bennett |
| 2005/0048538 A1 | 3/2005 | Mignot et al. |
| 2005/0061315 A1 | 3/2005 | Lee et al. |
| 2005/0061320 A1 | 3/2005 | Lee et al. |
| 2005/0061326 A1 | 3/2005 | Payne, Jr. |
| 2005/0075680 A1 | 4/2005 | Lowry et al. |
| 2005/0076906 A1 | 4/2005 | Johnson |
| 2005/0080461 A1 | 4/2005 | Stahmann et al. |
| 2005/0081854 A1 | 4/2005 | Nadjafizadeh et al. |
| 2005/0085738 A1 | 4/2005 | Stahmann et al. |
| 2005/0085874 A1 | 4/2005 | Davies et al. |
| 2005/0090871 A1 | 4/2005 | Cho et al. |
| 2005/0108133 A1 | 5/2005 | Hsu et al. |
| 2005/0113646 A1 | 5/2005 | Sotos et al. |
| 2005/0113710 A1 | 5/2005 | Stahmann et al. |
| 2005/0119285 A1 | 6/2005 | Matos et al. |
| 2005/0126574 A1 | 6/2005 | Wood |
| 2005/0133026 A1 | 6/2005 | Seleznev et al. |
| 2005/0143617 A1 | 6/2005 | Auphan |
| 2005/0148893 A1 | 7/2005 | Misczynski et al. |
| 2005/0148897 A1 | 7/2005 | Cho et al. |
| 2005/0149146 A1 | 7/2005 | Boveja et al. |
| 2005/0150504 A1 | 7/2005 | Heeke et al. |
| 2005/0215947 A1 | 9/2005 | Heruth et al. |
| 2005/0240253 A1 | 10/2005 | Tyler et al. |
| 2005/0258242 A1 | 11/2005 | Zarembo |
| 2005/0277999 A1 | 12/2005 | Strother et al. |
| 2006/0095078 A1 | 5/2006 | Tronnes |
| 2006/0095088 A1 | 5/2006 | De Ridder |
| 2006/0122653 A1 | 6/2006 | Bradley et al. |
| 2006/0149337 A1 | 7/2006 | John |
| 2006/0212096 A1 | 9/2006 | Stevenson |
| 2006/0224211 A1* | 10/2006 | Durand ............... A61N 1/3601 607/48 |
| 2007/0021794 A1 | 1/2007 | Kieval et al. |
| 2007/0043398 A1 | 2/2007 | Ternes et al. |
| 2007/0055308 A1 | 3/2007 | Haller et al. |
| 2007/0066997 A1 | 3/2007 | He et al. |
| 2007/0100399 A1 | 5/2007 | Parramon et al. |
| 2007/0100411 A1 | 5/2007 | Bonde |
| 2007/0129769 A1 | 6/2007 | He et al. |
| 2007/0150006 A1 | 6/2007 | Libbus et al. |
| 2007/0150022 A1 | 6/2007 | Ujhazy et al. |
| 2007/0173893 A1 | 7/2007 | Pitts |
| 2007/0179557 A1 | 8/2007 | Maschino et al. |
| 2007/0233204 A1* | 10/2007 | Lima ............... A61N 1/0551 607/46 |
| 2007/0255366 A1 | 11/2007 | Gerber et al. |
| 2007/0255367 A1 | 11/2007 | Gerber et al. |
| 2007/0288064 A1 | 12/2007 | Butson et al. |
| 2008/0021506 A1 | 1/2008 | Grocela et al. |
| 2008/0039904 A1 | 2/2008 | Bulkes et al. |
| 2008/0039916 A1 | 2/2008 | Colliou et al. |
| 2008/0091246 A1 | 4/2008 | Carey et al. |
| 2008/0097554 A1 | 4/2008 | Payne et al. |
| 2008/0103407 A1 | 5/2008 | Bolea et al. |
| 2008/0103544 A1 | 5/2008 | Weiner |
| 2008/0103545 A1 | 5/2008 | Bolea et al. |
| 2008/0109046 A1* | 5/2008 | Lima ............... A61N 1/0551 607/42 |
| 2008/0109047 A1 | 5/2008 | Piess |
| 2008/0114230 A1 | 5/2008 | Addis |
| 2008/0139913 A1 | 6/2008 | Schulman |
| 2008/0147141 A1* | 6/2008 | Testerman ......... A61N 1/36085 607/48 |
| 2008/0172109 A1 | 7/2008 | Rahman et al. |
| 2008/0288025 A1 | 11/2008 | Peterson |
| 2009/0118796 A1 | 5/2009 | Chen et al. |
| 2009/0210042 A1 | 8/2009 | Kowalczewski |
| 2009/0270904 A1 | 10/2009 | Birk et al. |
| 2010/0139667 A1 | 6/2010 | Atkinson et al. |
| 2011/0112604 A1 | 5/2011 | Meadows et al. |
| 2011/0213438 A1 | 9/2011 | Lima et al. |

FOREIGN PATENT DOCUMENTS

| | | |
|---|---|---|
| WO | 199900058 A1 | 1/1999 |
| WO | 2002087433 A1 | 11/2002 |
| WO | 2007092330 A1 | 8/2007 |
| WO | 2007098200 A2 | 8/2007 |
| WO | 2007098202 A2 | 8/2007 |
| WO | 2007117232 A1 | 10/2007 |
| WO | 2007140584 A1 | 12/2007 |
| WO | 2008005903 A2 | 1/2008 |
| WO | 2008039921 A2 | 4/2008 |
| WO | 2008046190 A1 | 4/2008 |
| WO | 2008048471 A2 | 4/2008 |
| WO | 2008049199 A1 | 5/2008 |
| WO | 2009048580 A1 | 4/2009 |
| WO | 2009048581 A1 | 4/2009 |

(56) References Cited

FOREIGN PATENT DOCUMENTS

| WO | 2009140636 A2 | 11/2009 |
|----|---------------|---------|
| WO | 2010039853 A1 | 4/2010 |
| WO | 2010059839 A2 | 5/2010 |

OTHER PUBLICATIONS

Office Action dated Mar. 27, 2012 in connection with U.S. Appl. No. 12/681,799.
Office Action dated Mar. 9, 2012 for U.S. Appl. No. 12/787,206.
Examiner's Report from Australian Patent Application No. 2007217783 dated Jul. 25, 2011.
Fairbanks, David W., M.D.; Fairbanks, David N.F., M.D.; Neurostimulation for Obstructive Sleep Apnea: Investigations; ENT Journal; Jan. 1993; pp. 52-57; vol. 72, No. 1; International Pub. Group; Cleveland, OH.
Final Office Action dated Nov. 4, 2010 in connection with U.S. Appl. No. 11/707,104.
Non-Final Office Action dated Nov. 5, 2010 in connection with U.S. Appl. No. 12/752,931.
International Search Report from International Application No. PCT/US2010/036070, dated Jul. 21, 2010.
Written Opinion of the International Search Authority Application No. PCT/US2010/036070, dated Jul. 21, 2010.
Office Action from U.S. Appl. No. 11/707,104 dated Jun. 21, 2010.
Gilliam, Edwin E. and Goldberg, Stephen J., Contractile Properties of the Tongue Muscles: Effects of Hypoglossal Nerve and Extracellular Motoneuron Stimulation in Rat, Journal of Neurophysiology, vol. 74, No. 2, Aug. 1995, pp. 547-555.
Nagai, et al., Effect of Aging on Tongue Protrusion Forces in Rats; Dysphagia (2008) 23:116-121.
Pae, Eung-Kwon et al., Short-Term Electrical Stimulation Alters Tongue Muscle Fibre Type Composition; Archives of Oral Biology, vol. 52, Issue 6 (Jun. 2007) 544-551.
Schwartz, et al., Therapeutic Electrical Stimulation of the Hypoglossal Nerve in Obstructive Sleep Apnea, Arch Otolarynogol Head Neck Surg., vol. 127. Oct. 2001, pp. 1216-1223.
Davis, et al., Development of the Bion® Microstimulator for Treatment in Obstructive Sleep Apnea, Alfred Mann Foundation, Valencia, California, Jul. 1-5, 2003 IFESS.
Sutlive, et al., Contractile Properties of the Tongue's Genioglossus Muscle and Motor Units in the Rat, Genioglossus Muscle Properties, Muscle & Nerve, Mar. 2000 pp. 416-425.
Sutlive, et al., Whole-Muscle and Motor-Unit Contractile Properties of the Styloglossus Muscle in Rat, The American Physiological Society, 1999, pp. 584-592.
Smith et al., Phenotype and Contractile Properties of Mammalian Tongue Muscles Inervated by the Hypoglossal Nerve, Respiratory Physiology and Neurobiology 147 (Feb. 23, 2005) 253-262.
Sawczuk et al., Neural Control of Tongue Movement With Respect RO Respiration and Swallowing, Crit Rev Oral Viol Med, 12(1): 18-37 (2001).
Goding, Jr., et al., Relife of Upper Airway Obstruction With Hypoglossal Never Stimulation in the Canine, The Larynogscope, Feb. 1998, 108:2, pp. 162-169.
Weiss, Implications of Silicon Monolithic RFICs for Medical Instrumentation and Telemetry, IEEE, 1998 pp. 195-204.
Troyk, Injectible Electronic Identification, Monitoring, and Stimulation Systems, Annu. Rev. Biomed. Eng. 1999, 01:177-209.
Sahin et al., Closed-Loop Stimulation of Hypoglossal Nerve in a Dog Model of Upper Airway Obstruction, IEEE Transactions on Biomedical Engineering, vol. 47, No. 7, pp. 919-925, Jul. 2000.
Yoo et al., Selective Stimulation of the Hypoglossal Nerve With a Multi-Contact Cuff Electrode, 2001 IEE, pp. 1309-1312.
Yoo et al., Selective Stimulation of the Hypoglossal Nerve: a Fine Approach to Treating Obstructive Sleep Apnea, 2002 IEEE, pp. 2049-2050.
Eisele, M.D., et al., Tongue Neuromuscular and Direct Hypoglossal Nerve Stimulation of Obstructive Sleep Apnea, Otolarynogol Clin N. Am 36 92003) 501-510.
Tran et al., Development of Asynchronous, Intralingual Electrial Stimulation to Treat Obstructive Sleep Apena, 2003 IEEE pp. 375-378.
Huang et al., Activation Patterns of the Tongue Muscles With Selective Stimulation of the Hyroglossal Nerve, 2004 IEEE, pp. 4275-4278.
Arndt, Rewiring the Body, BusinessWeek, Mar. 7, 2005, 99 74-82.
Yoo et al., a Neural Prosthesis for Obstructive Sleep Apnea, 2005 IEEE, pp. 5254-5256.
Wells, the Sleep Racket Who's Making Big Bucks Off Your Insomnia? Forbes, Feb. 27, 2006, pp. 80-88.
International Search Report for PCT/US2007/04512 dated Nov. 29, 2007.
International Search Report for PCT/US2008/011598 dated Dec. 12, 2008.
International Search Report for PCT/US2008/011599 dated Dec. 12, 2008.
Office Action dated Aug. 28, 2009 for U.S. Appl. No. 11/707,053.
International Search Report for PCT/US2009/59374 dated Dec. 3, 2009.
Huang, J. et al.: "Dilation of the oropharynx via selective stimulation of the hypoglossal nerve", Journal of Neural Engineering, vol. 2, No. 4, Aug. 2005, pp. 73-80.
Office Action dated Jan. 27, 2016 for Canadian Patent Application No. 2,641,821.

* cited by examiner

APPARATUS, SYSTEM, AND METHOD FOR SELECTIVE STIMULATION

CROSS REFERENCE TO RELATED APPLICATIONS

This application is a continuation of U.S. patent application Ser. No. 12/681,812, which is a National Stage Patent Application of International Application No. PCT/US2008/011598, filed Oct. 9, 2008, which claims the benefit of U.S. Patent Application Nos. 60/978,519 and 61/017,614 and 61/136,102, filed on Oct. 9, 2007 and Dec. 29, 2007 and Aug. 12, 2008 respectively, which are all incorporated herein by reference in their entirety.

FIELD OF THE INVENTION

The present invention relates to an apparatus, system, and method for implantable therapeutic treatment of a patient.

BACKGROUND OF THE INVENTION

Acute and chronic conditions such as pain, arthritis, sleep apnea, seizure, incontinence, and migraine are physiological conditions affecting millions of people worldwide. For example, sleep apnea is described as an iterated failure to respire properly during sleep. Those affected by sleep apnea stop breathing during sleep numerous times during the night. There are two types of sleep apnea, generally described in medical literature as central and obstructive sleep apnea. Central sleep apnea is a failure of the nervous system to produce proper signals for excitation of the muscles involved with respiration. Obstructive sleep apnea (OSA) is caused by physical obstruction of the upper airway channel (UAW).

Current treatment options range from drug intervention, non-invasive approaches, to more invasive surgical procedures. In many of these instances, patient acceptance and therapy compliance is well below desired levels, rendering the current solutions ineffective as a long-term solution.

Implants are a promising alternative to these forms of treatment. For example, pharyngeal dilation via hypoglossal nerve (XII) stimulation has been shown to be an effective treatment method for OSA. The nerves are stimulated using an implanted electrode. In particular, the medial XII nerve branch (i.e., in. genioglossus), has demonstrated significant reductions in UAW airflow resistance (i.e., increased pharyngeal caliber).

Implants have been used to treat other conditions as well. For example, stimulation of the vagus nerve is thought to affect some areas in the brain prone to seizure activity; sacral nerve stimulation is an FDA-approved electronic stimulation therapy for reducing urge incontinence; and stimulation of peripheral nerves may help treat arthritis pain.

While electrical stimulation of nerves has been experimentally shown to remove or ameliorate certain conditions (e.g., obstructions in the UAW), current implementation methods typically require accurate detection of a condition (e.g., a muscular obstruction of an airway), selective stimulation of a muscle or nerve, and a coupling of the detection and stimulation components. Additionally, attempts at selective stimulation have focused on activating entire nerves or nerve bundles. A need therefore exists for an apparatus and method for selectively activating only the portion of the nerve responsible for activating the desired muscle or muscle groups while avoiding activation of unwanted muscles or muscle groups.

Accordingly, the present invention is directed to an apparatus, system, and method for selective stimulation that substantially obviates one or more problems due to limitations and disadvantages of the related art.

SUMMARY OF THE INVENTION

The present invention includes an implantable neurostimulator system with a hollow cylindrical electronics enclosure having a top, a bottom, and a side; a coil extending from a first part of the electronics enclosure; and at least one electrode operatively connected to the electronics enclosure.

In another embodiment, an implantable neurostimulator system includes a symmetrical chevron-shaped molded body having an apex, a first and second side, and a base; a coil at the apex of the molded body; an electronics enclosure at least partially integral with the molded body; and at least one electrode operatively connected to the electronics enclosure.

In a further embodiment, an implantable neurostimulator system includes an electronics enclosure; a coil; and at least one perforated cuff electrode operatively connected to the electronics enclosure.

In yet another embodiment, an implantable neurostimulator system includes an electronics enclosure; a coil; and at least one flat-bottomed open trough electrode operatively connected to the electronics enclosure.

Another embodiment of the invention includes an apparatus and method of neurostimulation, the method including the steps of at least partially encircling a nerve with a cuff having a first and second surface, the cuff having at least one contact on one of the first and second surfaces; connecting at least one stimulus generator to the at least one contact; and delivering a stimulus to the at least one contact.

It is to be understood that both the foregoing general description and the following detailed description are exemplary and explanatory, and are intended to provide further explanation of the claimed invention.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention. In the drawings.

DETAILED DESCRIPTION OF THE INVENTION

Reference will now be made in detail to the embodiments of the present invention, examples of which are illustrated in the accompanying drawings. Wherever possible, like reference numbers are used for like elements.

It is to be understood that both the foregoing general description and the following detailed description are exemplary and explanatory and are intended to provide further explanation of the invention as claimed. Additional features and advantages of the invention will be set forth in the description that follows, and in part will be apparent from the description, or may be learned by practice of the invention. The objectives and other advantages of the invention will be realized and attained by the structure particularly pointed out in the written description and claims hereof as well as the appended drawings.

According to some embodiments, an implantable neurostimulator system of the present invention includes an implantable pulse generator system (IPG); and at least one electrode operatively connected to the IPG to generate accurate, selective nerve stimulation patterns. Exemplary components of various embodiments of the claimed invention are described hereafter.

I. Implantable Pulse Generator Systems (IPGs)

Implantable pulse generator systems (IPGs) include one or more of (1) an implant (e.g., FIGS. 1A-2D); (2) a power system (e.g., FIGS. 4A-4D); and (3) an IPG accessory (e.g., FIGS. 5A-5D). Examples of each are discussed below.

A. Exemplary IPG Implants

FIGS. 1A-2D illustrate exemplary embodiments of IPG implants. Referring to FIGS. 1A-1F, an embodiment of the IPG system includes a mastoid bone implant 100. Referring to FIGS. 2A-2D, another embodiment of the IPG system includes a sub-mandibular implant 200.

2. Mastoid Bone Implant

FIGS. 1A-1F illustrate a mastoid bone implant embodiment of an IPG for treating obstructive sleep apnea. In the exemplary embodiment shown in FIGS. 1A-1F, the mastoid bone implant 100 is implanted into the mastoid, which is a bony portion of the skull behind the ear. The mastoid bone bed is close to the HGN, and provides a stable well-protected location for the mastoid bone implant 100.

Figure 1A:
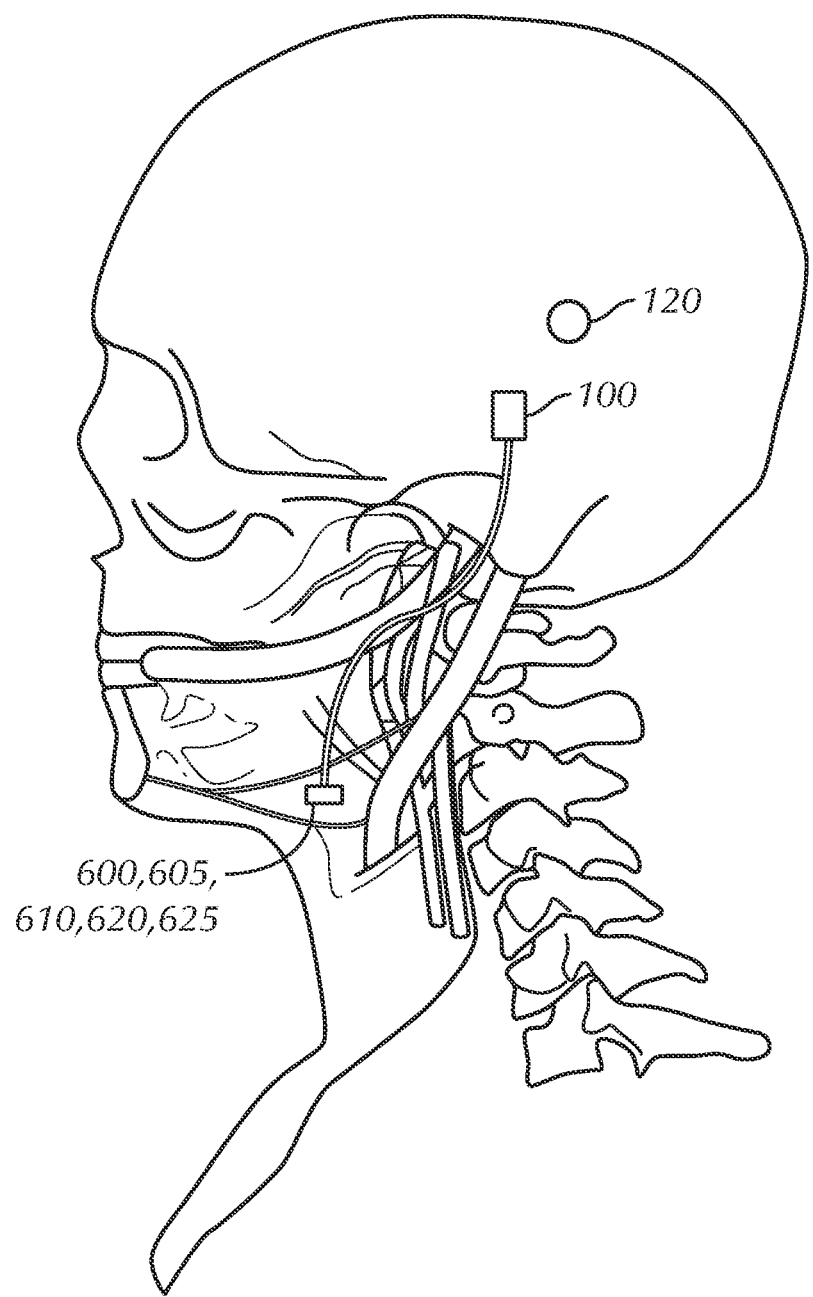
FIGS. 1A-1F show an exemplary embodiment of a mastoid bone implantable pulse generator (IPG) implant.
Figure 1B:
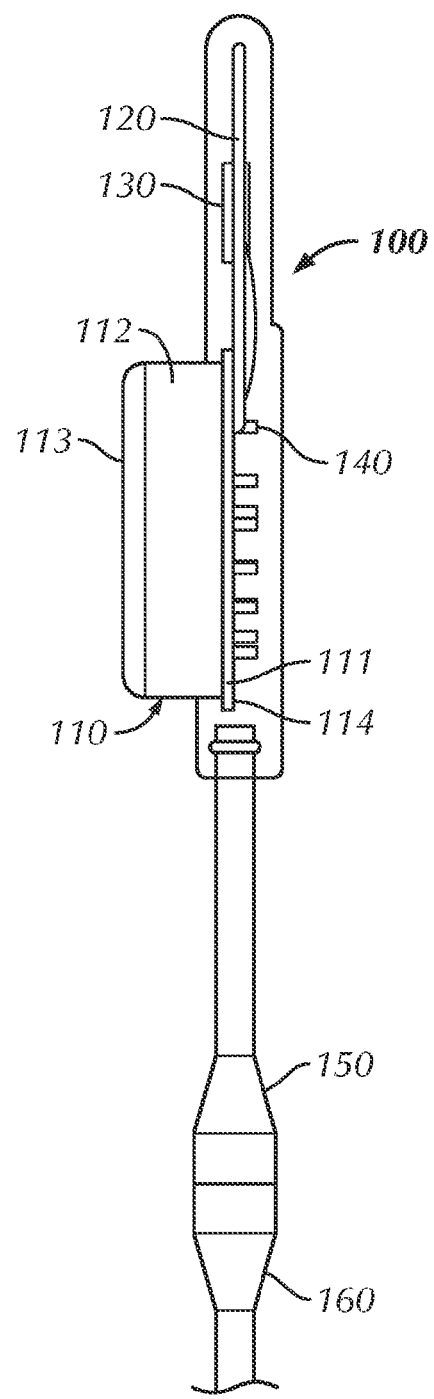
Figure 1C:
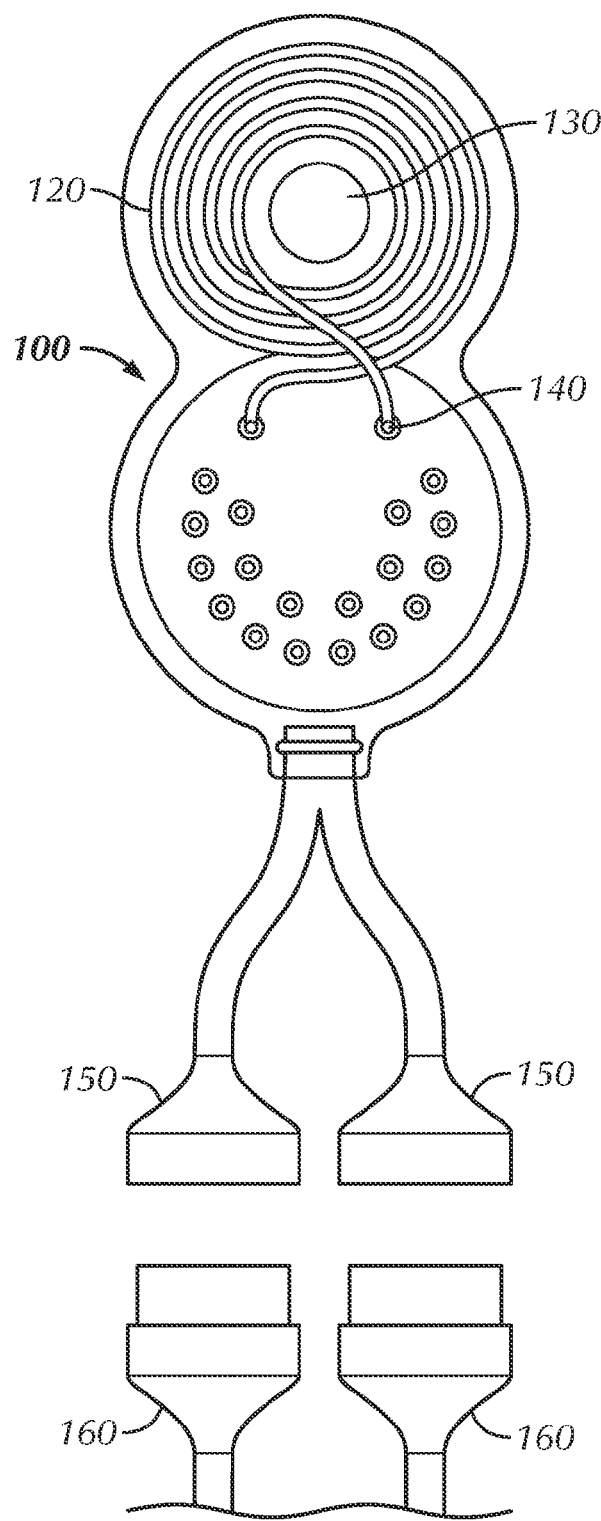
Figure 1D:
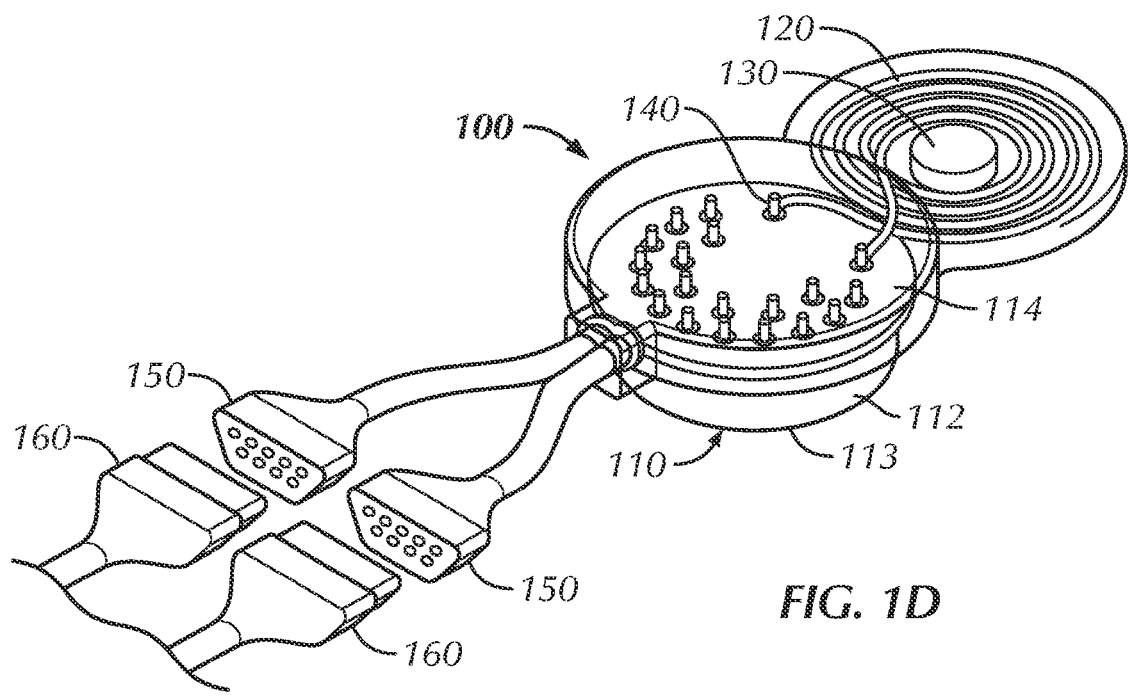
Figure 1E:
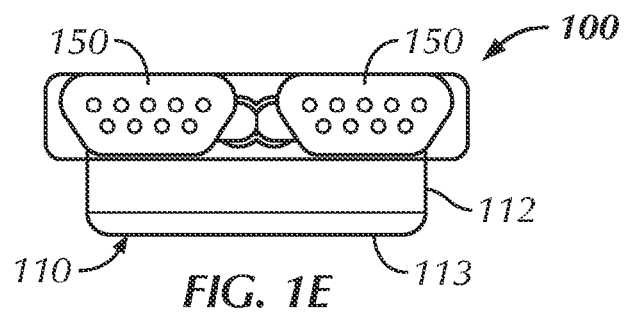
Figure 1F:
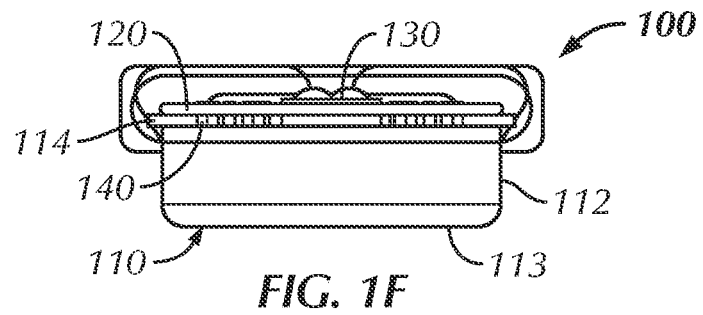
Figure 2A:
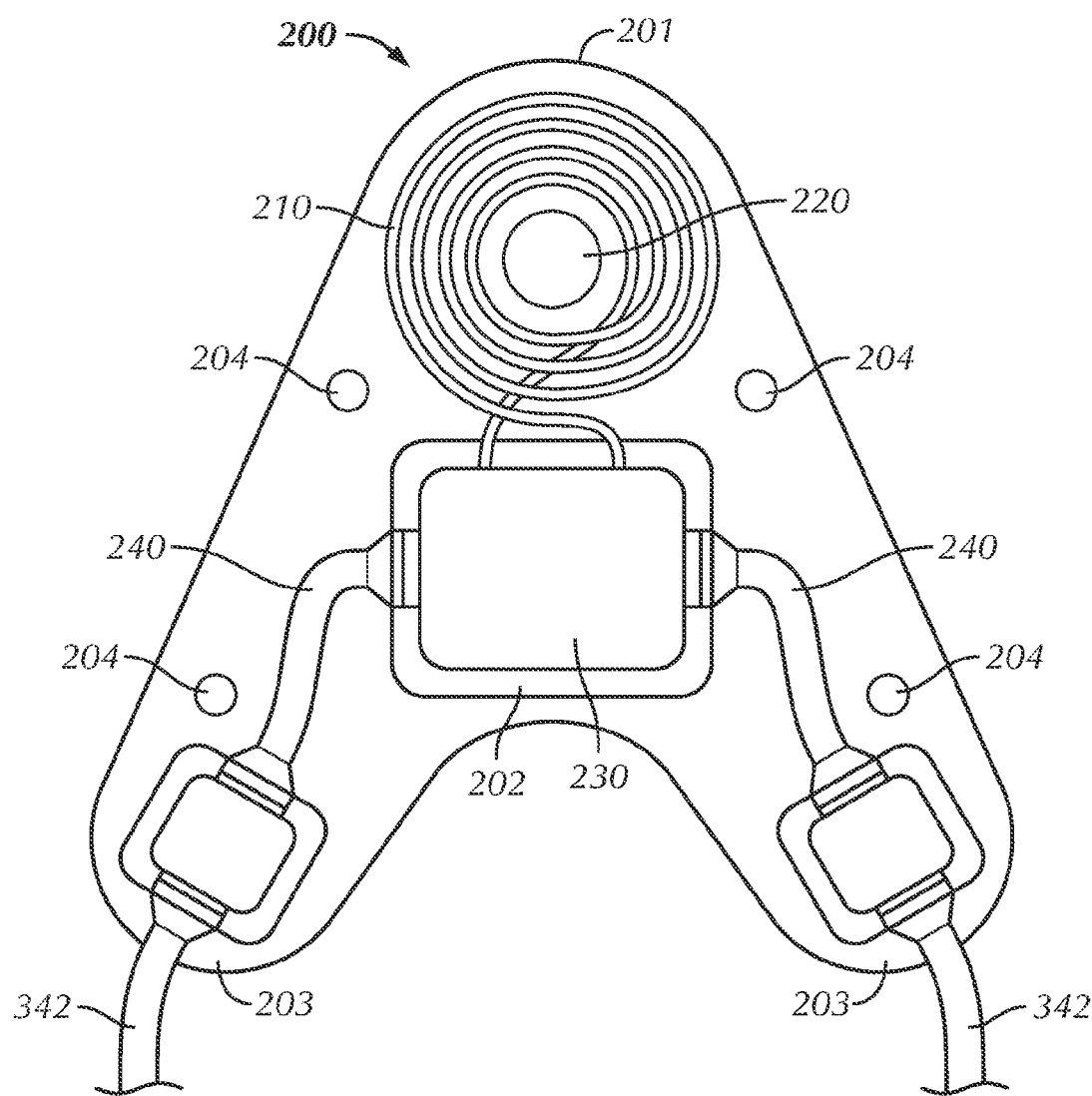
FIGS. 2A-2D show an exemplary embodiment of a submandibular implantable pulse generator (IPG) implant.
Figure 2B:
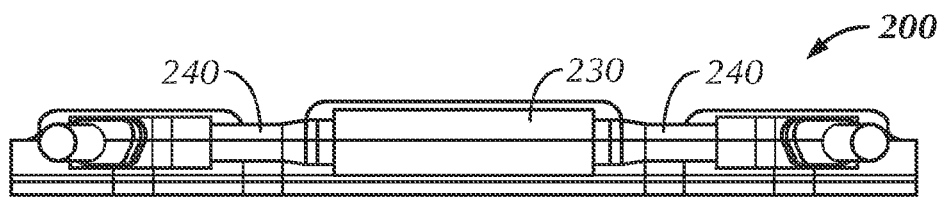
Figure 2C:
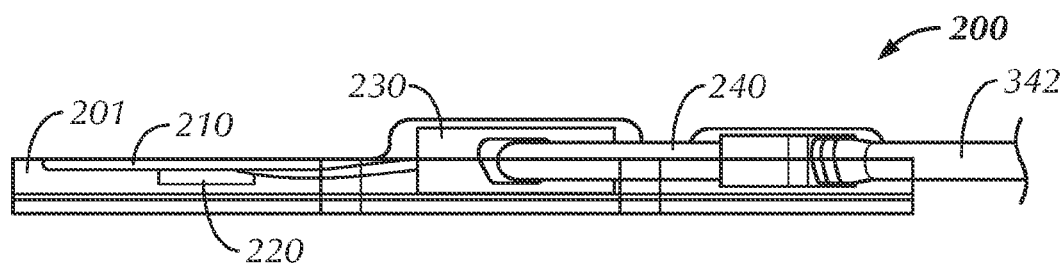
Figure 2D:
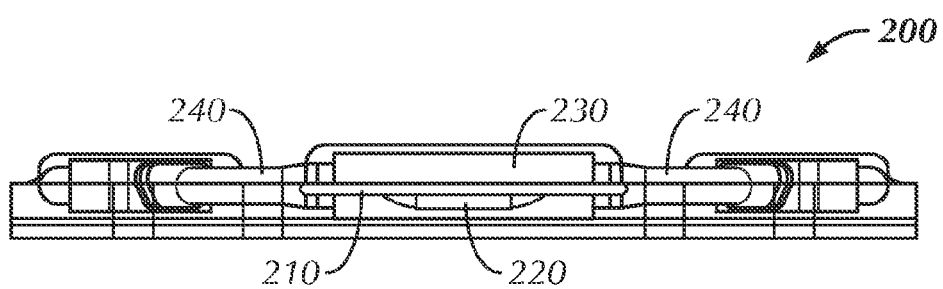

FIG. 1A illustrates an exemplary embodiment of a unilateral mastoid bone implant 100 implantable pulse generator system. This area is a common location for cochlear implants. The mastoid bone implant 100 is placed into a well that is surgically excavated in the mastoid bone below the surface of the skull to secure the implant in place. Placing the mastoid bone implant 100 in a well protects the implant, reduces the amount it protrudes from the skull, and provides a lower device profile.

The embodiment shown can be implanted to stimulate the left, right, or both HGNs. In a unilateral procedure, the mastoid bone implant 100 is typically located on the same side of the head as the HGN being stimulated. In a bilateral procedure, a tunnel is formed in the patient's neck from the mastoid bone implant 100 side to the opposite side for the second HGN lead and electrode. While only one electrode (discussed later) is shown in FIG. 1A, multiple electrodes may be used without departing from the scope of the invention.

a. Physical Configuration

In the exemplary embodiment shown in FIGS. 1A-1F, the mastoid bone implant 100 has a hollow cylindrical electronics enclosure 110 (also known as a case or a can) with a top 111, a bottom 113, and a side 112. The case 110 houses the implant electronics and power source. The case 110 is typically made of a biocompatible material, and may be hermetically sealed. In the embodiment shown, a lip 114 encircles at least a portion of the side 112 of the enclosure 110, and in certain embodiments has one or more holes to allow a surgeon to anchor the mastoid bone implant 100 in place with sutures.

In certain embodiments, silastic and/or silicone rubber (referred to generically as silastic) covers at least a portion of the electronics enclosure 110. Other materials known to those skilled in the art may be used without departing from the scope of the invention. In embodiments with a lip 114, the lip may be used to help secure the silastic to the enclosure 110. In certain embodiments, some or all of the remaining case exterior not covered with silastic acts as an electrode. The electronics enclosure 110 in FIGS. 1A-1F is exemplary only, and not limited to what is shown.

An internal coil 120 extends from a first part of the side 112 of the electronics enclosure 110. In the exemplary embodiment shown, the internal coil 120 receives power, and supports bidirectional data and command telemetry. The internal coil 120 is encased in silastic, which may have an internal Dacron mesh or similar cloth for added tear resistance and durability. Similar materials known to those skilled in the art can be used without departing from the scope of the invention.

Figure 5A:
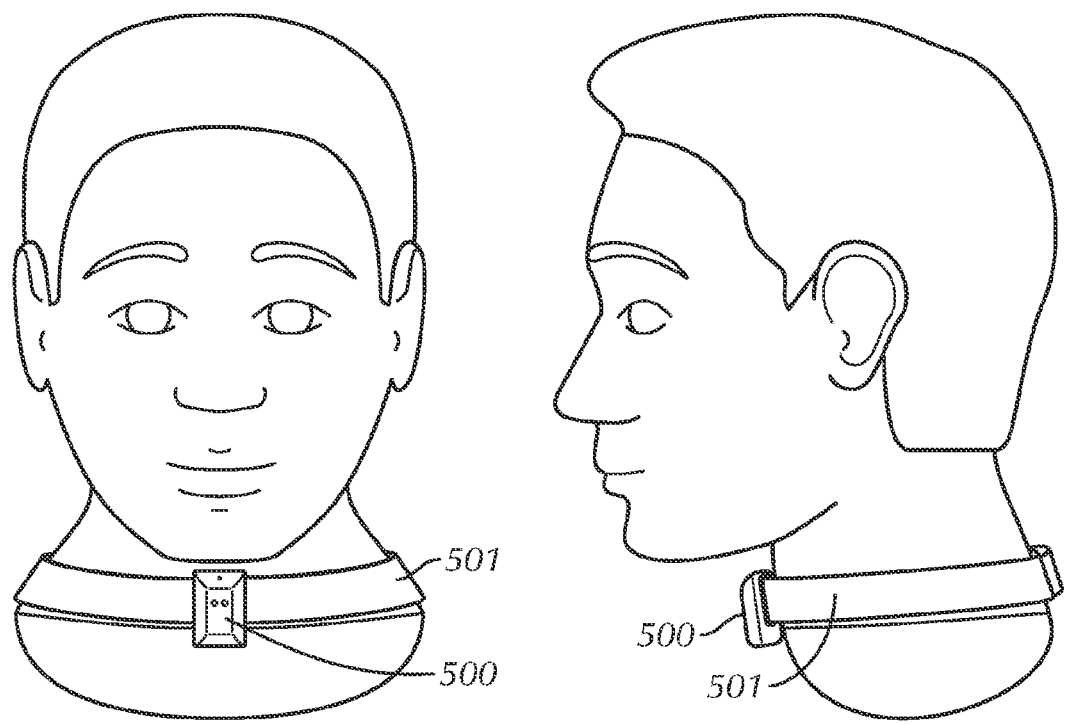
FIGS. 5A-5D show exemplary embodiments of IPG accessories.
Figure 5B:
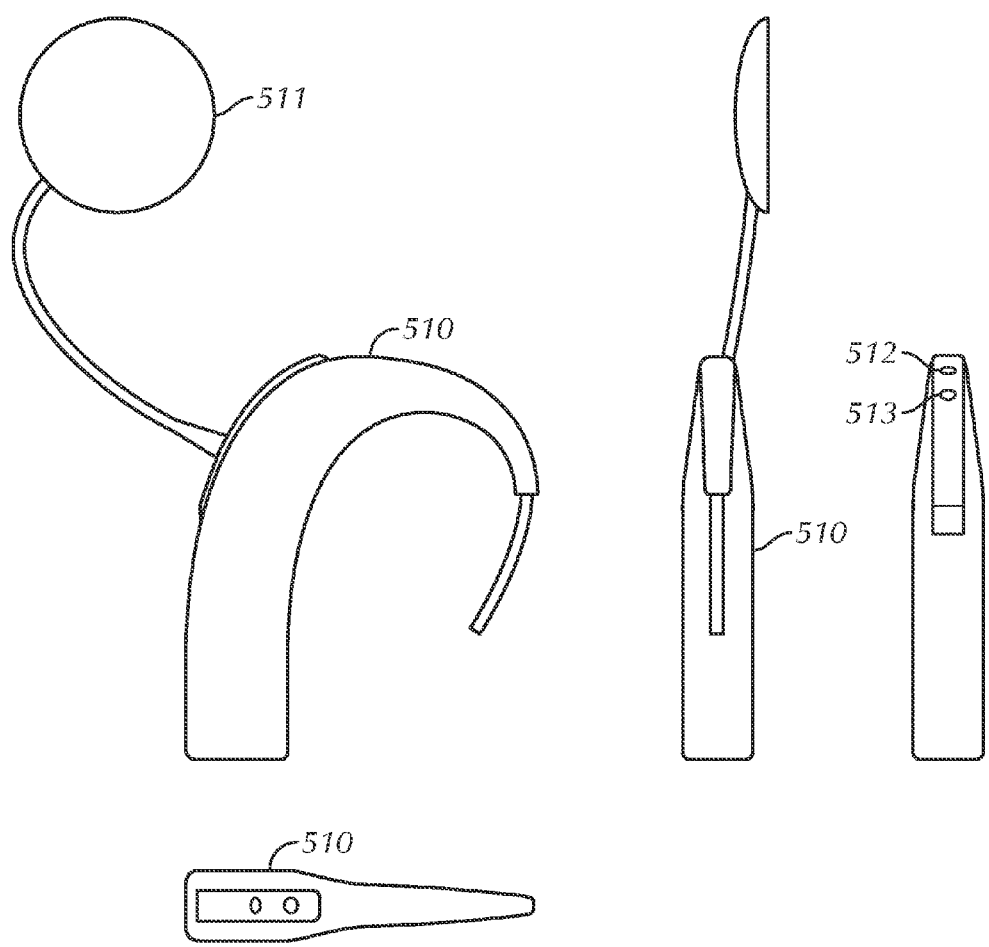

In certain embodiments, an internal magnet 130 helps align the internal coil 120 with an external coil 511 (FIG. 5B). The internal magnet 130 may be hermetically sealed, and in certain embodiments is embedded in the approximate center of the internal coil 120. In certain embodiments, a second magnet (not shown) is located in the external controller coil 511. The internal magnet 130 and external controller magnet (not shown) are oriented so that they are attracted to each other when the external controller coil is near the internal coil 120. The attractive force of the two magnets brings the two coils close together, helping to maintain alignment between the coils. Aligning the coils helps optimize power and telemetry data transfer between the external controller and the mastoid bone implant 100.

The mastoid bone implant 100 may be implanted to stimulate the left, right, or both HGNs. In certain embodiments, the mastoid bone implant 100 orientation affects the internal magnet 130 orientation. Therefore, in certain embodiments the internal magnet 130 in the mastoid bone implant 100 is reversible. In other exemplary embodiments, the internal magnet 130 is removable, for procedures such as an MRI where the presence of a strong magnet in the patient might affect the images obtained or the forces generated and applied to the implanted internal magnet 130 by the static magnetic field of the MRI system might be unsafe for the patient. In still other embodiments, the internal magnet 130 and/or external controller magnet may be replaced with a material that is attracted to a magnet, either to eliminate the magnet on one side of the pair of devices, or to provide a lower profile to the corresponding coil assembly.

b. Internal Components

In the embodiment shown in FIGS. 1A-1F, one or more glass-to-metal feedthrough leads 140 extend through the top of the electronics enclosure 110. In the exemplary embodiment shown, the leads 140 are encased in silastic or similar material. The location of the feedthrough leads 140 is exemplary only, and not limited to what is shown.

Feedthrough leads 140 at the top of the electronics enclosure 110 bring electrode and antenna connections from the enclosure 110 to the internal electronics. The feedthrough leads 140 shown are glass-to-metal feedthrough leads, but other non-conducting material known to those skilled in the art can be used in place of or in addition to glass to make the feedthrough leads 140. Gold or nickel wires connect case feedthrough pins to internal circuitry inside the enclosure 110. Stainless steel, platinum-iridium, gold or MP35N wires connect external portions of the feedthrough pins to connector, lead, or antenna connections external to the enclosure 110.

The electronics design within the case 110 varies, often depending on the implant power source. For example, referring to FIG. 4A, in an exemplary embodiment of an RF implant (discussed later), the implant uses an external controller and power source. Since the power source and controller are external to the implant, the internal electronics are relatively simple. The implant need not have volume for a battery or ultracapacitor, and with the controller external to the implant, control and stimulation functions may be reduced to such a significant extent that a state-machine design could realistically be utilized. This has the added advantage of reducing power consumption and hybrid assembly real estate area as well, but has the disadvantage of being a more inflexible design with future product changes requiring a new application-specific integrated circuit (ASIC) state machine design.

Other exemplary embodiments have their own power sources. These exemplary embodiments have means to charge and protect the internal power storage elements, and may have means to monitor these functions. Because of this added complexity, and because of the opportunity for independent operation without constant external supervision, the architecture of the IPG electronics may include a microcontroller along with the custom ASIC to generate the stimulus pulses and handle charging and telemetry functions. This has the added benefit of future functionality improvements along with field upgrade options for existing patients, as well as increased diagnostic functionality. In still other embodiments, the IPG electronics may include an acoustic pickup and sound processor to identify snoring. The snoring may be used as a trigger to initiate and/or modify stimulus patterns as the patient moves from one stage of sleep to another.

In still other embodiments, the mastoid bone implant 100 has an internal RF interface. In these embodiments, RF may be used to send power and/or control signals to the implant. The internal RF interface operates according to the principle of inductive coupling. The internal RF interface may also include a passive RFID transponder with a demodulator and a modulator. In certain embodiments, the RFID-based implant exploits the near-field characteristics of short wave carrier frequencies of approximately 13.56 MHz. In yet another embodiment, the RFID-based implant uses frequencies between 10 and 15 MHz. This carrier frequency may be further divided into at least one sub-carrier frequency.

The internal RF interface may also have a number of other characteristics. For example, the internal RF interface may include one or more of a transponder, internal antenna, modulator, demodulator, clock, and rectifier. The transponder may be passive or active. Furthermore, the transponder may have further separate channels for power delivery and data and control, and in some embodiments, the transponder may employ a secure full-duplex data protocol. The RF interface may further include an inductive coupler, an RF to DC converter, and an internal antenna, and the antenna may include a magnetic component. In other embodiments, the internal RF interface can send and/or receive control logic and/or power.

In some embodiments, the internal RF interface uses a sub-carrier frequency for communication with an external RF interface that may be located, for example, in an external controller. The sub-carrier frequency may be used for communication between the internal and external RF interfaces and is obtained by the binary division of the external RF interface carrier frequency. The transponder may use the sub-carrier frequency to modulate a signal back to the external RF interface.

c. Connectors

As shown in FIGS. 1B-1F, one or more multi-contact implant connectors 150 extending from a second part of the side 112 of the electronics enclosure 110 opposite the coil 120 connect electrode lead connectors 160 with cables having one or more electrode leads to the mastoid bone implant 100. The type of connector, number of pins, and the location of the connectors are exemplary only, and not limited to what is shown.

In one embodiment, the implant connector 150 is a five to nine position female connector, which mates to corresponding lead pins in the electrode lead connector 160. These electrode lead connections 160 extend from cables having one or more electrode leads that connect with electrode contact connections for four to eight cathodic contacts and a single or array of common anodes. This configuration allows stimulation to occur between any two or more independent contacts and/or the case 110. The receptacles are made of a biocompatible material such as stainless steel, titanium, or MP35N, and arranged in a staggered row or other configuration to reduce space.

In certain embodiments, molded silicone rubber provides a detent feature to the female implant connector 150, which helps hold the male portion of the electrode lead connector 160 in place. Male portions of the electrode lead connectors 160 optionally have a taper feature providing strain relief to the lead to prevent stress fracture failures in the lead wires. If a connector is unused, as, for example, in a unilateral implant for a single HGN, it is protected with a dummy plug (not shown) to prevent tissue ingrowth and isolate any unused contacts from bodily fluids.

Certain embodiments include suture holes on the connector areas. The suture holes help the surgeon lock the connectors together. If used, the sutures help tighten the connection between the male and female connectors. As a non-limiting example, the surgeon may suture around the shroud around the female and male assembled connection to tighten the connection between elements. Other methods known to those skilled in the art may be used without departing from the scope of the invention.

2. Sub-Mandibular IPG Implant

FIGS. 2A-2D illustrate an embodiment of a sub-mandibular IPG implant 200 for treating obstructive sleep apnea (OSA). In this embodiment, the sub-mandibular implant 200 stimulates the hypoglossal nerve (HGN), a peripheral nerve located below and behind the lower mandible. The HGN is typically 4 to 5 mm in diameter, with a typical epineurium thickness of less than 1 mm. In the embodiment shown, the sub-mandibular implant 200 may be placed within the sub-mandibular space. There is minimal nerve motion in this area during sleep. There, the sub-mandibular implant 200, attached leads 342 (FIGS. 3B-3C) (discussed later), and electrodes (FIGS. 6A-6G) (discussed later) are protected from jaw and neck movement relative to the tissues adjacent to the implanted elements. This helps secure the sub-mandibular implant 200 in place and prevent migration and drooping into the neck region. The sub-mandibular implant 200 is minimally invasive and easily implanted.

a. Physical Configuration

In the exemplary embodiment shown in FIGS. 2A-2D, the sub-mandibular implant 200 is chevron-shaped, roughly triangular with the base 202 of the triangle pulled upwards toward the apex 201 of the triangle, with smooth corners 203 and a small surface area. The apex 201 and corners 203 of the sub-mandibular implant 200 are curved to eliminate sharp corners that may harm a patient. The chevron shape helps the sub-mandibular implant 200 fit within the sub-mandibular space. One or more holes 204 along each side of the chevron apex 201 optionally allow a surgeon to anchor the sub-mandibular implant 200 in place with sutures. If used, the sutures connect to the fascia attached to the bottom and inner surfaces of the mandible, to help secure the sub-mandibular implant 200 in place and prevent migration and drooping into the neck region. Because of its shape, the sub-mandibular implant 200 may be implanted to stimulate the left, right, or both HGNs. The sub-mandibular implant 200 orientation with respect to the target HGN is the same on either HGN, meaning that the sub-mandibular implant 200 cannot be incorrectly implanted with respect to its inside or outside surface, enabling efficient power and data transfer in any configuration.

In the embodiment shown, the bulk of the sub-mandibular implant 200 is silastic and/or silicone rubber (generically referred to as silastic) with an internal Dacron mesh or similar cloth to add tear resistance and durability to the package. These materials are exemplary only, and not limited to what is shown. Other materials known to those skilled in the art may be used without departing from the scope of the invention.

b. Internal Components

In the embodiment shown in FIGS. 2A-2D, an internal coil 210 lies at the apex 201 of the sub-mandibular implant 200. With the internal coil 210 located as shown, it is not sensitive to orientation. It functions equally well whether implanted on the right or left HGN. The internal coil 210 receives power, and supports bidirectional data and command telemetry. The internal coil 210 shown is made of gold or platinum wire, but may be made from other conductive materials known to those skilled in the art without departing from the scope of the invention.

In certain embodiments, an internal magnet 220 helps align the internal coil 210 with an external coil 511 (FIG. 5B). The internal magnet 220 may be hermetically sealed, and in certain embodiments is embedded in the approximate center of the internal coil 210. In certain embodiments, a second magnet (not shown) is located in the external controller coil 511. The internal 220 and external 520 controller magnets are oriented so that they are attracted to each other when the external controller coil 511 is near the internal coil 210. The attractive force of the two magnets brings the two coils close together, helping to maintain alignment between the coils. Aligning the coils helps optimize power and telemetry data transfer between the external controller and the sub-mandibular implant 200.

As previously discussed, the sub-mandibular implant 200 may be implanted to stimulate the left, right, or both HGNs. In certain embodiments, sub-mandibular implant 200 orientation affects the internal magnet 220 orientation. Therefore, in certain embodiments the internal magnet 220 in the sub-mandibular implant 200 is reversible. In other exemplary embodiments, the internal magnet 220 is removable, for procedures such as an MRI where the presence of a strong magnet in the patient might affect the images obtained or the forces generated and applied to the implanted internal magnet 220 by the static magnetic field of the MRI system might be unsafe for the patient. In still other embodiments, the internal magnet 220 and/or external controller magnet (not shown) may be replaced with a material that is attracted to a magnet, either to eliminate the magnet on one side of the pair of devices, or to provide a lower profile to the corresponding coil assembly.

In one embodiment shown in FIGS. 2A-2D, just below the internal coil 210, at the base 202 of the chevron, lies an electronics enclosure (the case) 230 housing the implant electronics and power source. In the embodiment shown, silastic covers at least a portion of the case 230. In certain embodiments, at least a portion of the case 230 surface is left exposed to act as an electrode. The case 230 location is exemplary only, as is the portion of the case 230 covered with silastic, and not limited to what is shown.

The case 230 is typically made of biocompatible metal, such as a 6-4 titanium alloy. A titanium alloy is chosen because of its high resistivity compared to commercially pure (CP) titanium. The higher resistivity helps minimize power losses due to eddy currents resulting from exposure to RF fields, such as a charging field. Other biocompatible materials may be used without departing from the scope of the invention. In certain embodiments, the electronics enclosure 230 is hermetically sealed. The enclosure 230 may be any hermetic enclosure known to those skilled in the art.

Feedthrough leads 240 in the sides of the electronics enclosure 230 bring electrode and antenna connections from the enclosure 230 to the internal electronics. The feedthrough leads 240 shown are glass-to-metal feedthrough leads, but other non-conducting material known to those skilled in the art can be used in place of or in addition to glass to make the feedthrough leads 240. Gold or nickel wires connect case feedthrough pins to internal circuitry inside the enclosure 230. Stainless steel, platinum-iridium, gold or MP35N wires connect external portions of the feedthrough pins to connector, lead, or antenna connections external to the enclosure 230. In certain embodiments, such as the embodiment shown in FIG. 3A (discussed later), at least one permanently attached electrode lead 341 (FIG. 3A) connects the electrodes and antenna to the sub-mandibular implant 200. Using permanently attached electrode leads 341 rather than connectors 350 increases system reliability.

The electronics design within the case 230 varies, often depending on the implant power source. Examples of how the electronics design varies with the power source are described in the sections discussing the mastoid bone implant 100 (above) and are not repeated here.

c. Connectors

Figure 3A:
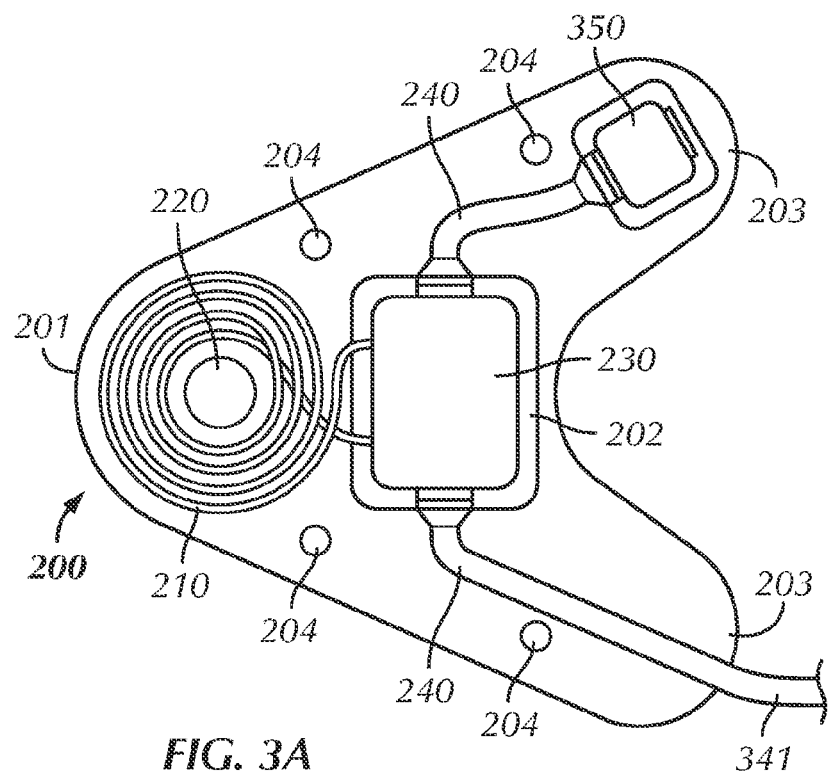
FIGS. 3A-3C show exemplary embodiments of IPG cables and connectors.
Figure 3B:
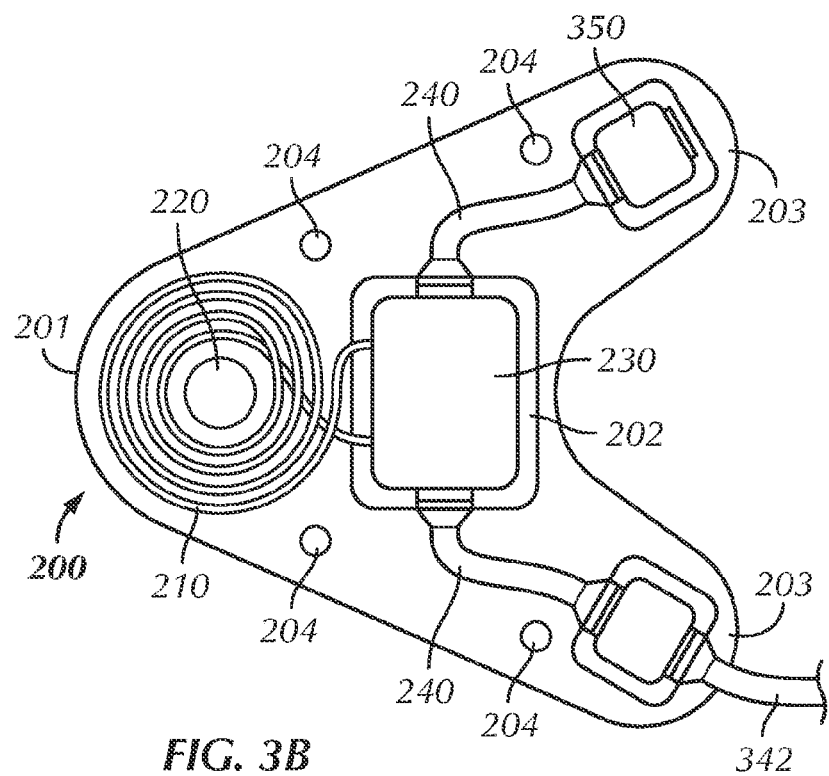
Figure 3C:
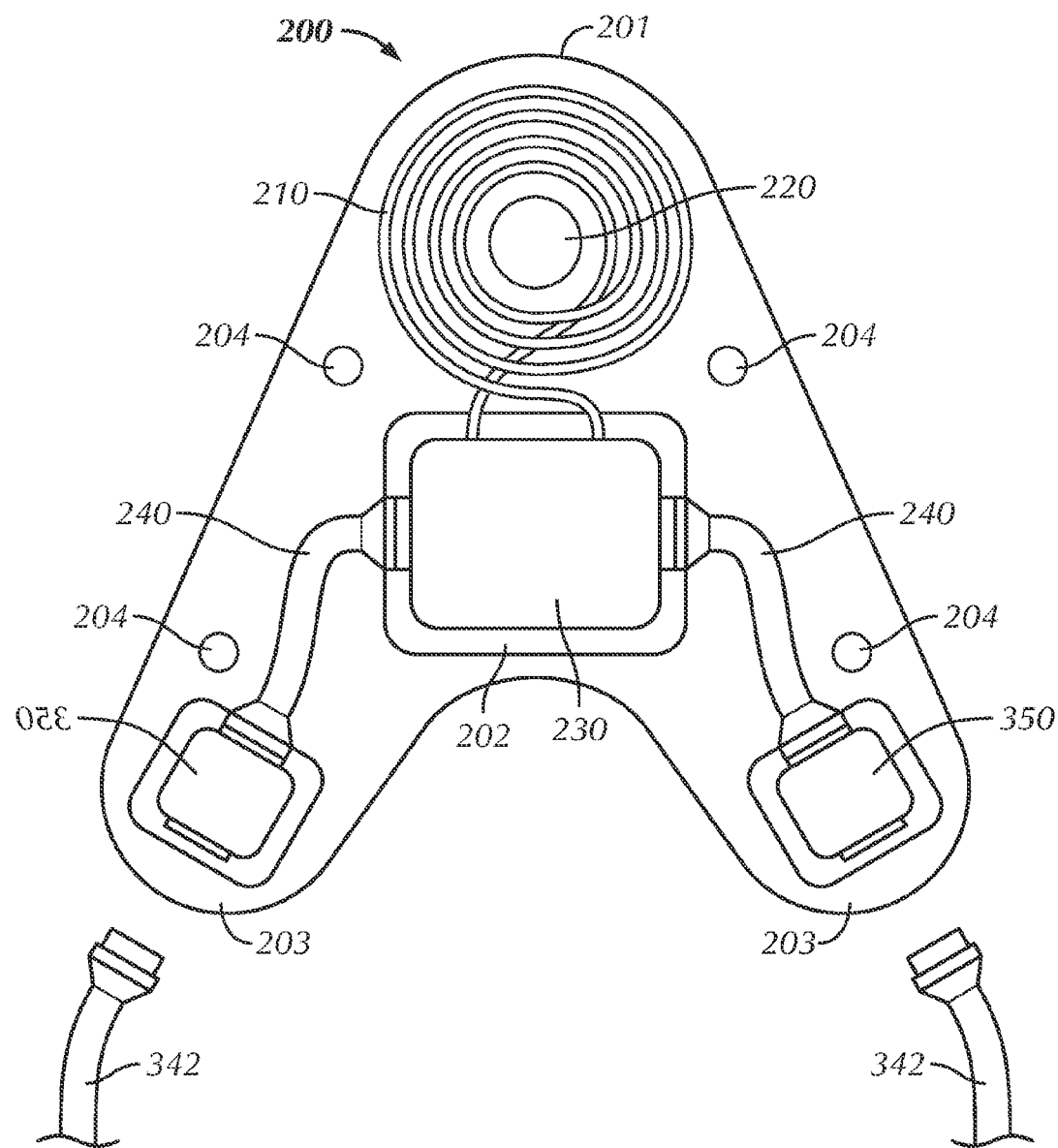

FIGS. 3A-3C show exemplary embodiments of IPG electrode leads 341, 342 and multi-contact implant connectors 350. Although shown with a sub-mandibular implant 200, they may also be used with a mastoid bone implant 100. The implant connectors 350 connect electrode leads 341, 342 and electrodes to the sub-mandibular implant 200. The electrode leads 341, 342 and electrodes connect to the implant connectors 350 with lead wires having polyurethane, silicone rubber, or similar insulating material, and wiring made from stainless steel, MP35N, titanium, 90/10 Pt—Ir, gold, or other material with high conductivity, high fatigue resistance, and good tensile properties. The lead wires have high biocompatibility and high corrosion resistance in implanted stimulation conditions. In certain exemplary embodiments, the wire material is MP35N drawn-filled-tube (DFT) with a silver core. This material has excellent fatigue resistance and high tensile strength, and the silver core lowers its electrical resistance to more desirable levels.

In one embodiment, the implant connector 350 is a five to nine position female connector, which mates to corresponding lead pins in the electrode lead 341, 342. These electrode leads 341, 342 connect with electrode contact connections for four to eight cathodic contacts and a single or array of common anodes. This configuration allows stimulation to occur between any two or more independent contacts and/or the case 230. The receptacles are made of a biocompatible material such as stainless steel, titanium, or MP35N, and arranged in a staggered row or other configuration to reduce space. One or more multi-contact implant connectors 350 on at least one corner of the sub-mandibular implant 200 connect electrode leads 341, 342 to the sub-mandibular implant 200.

In the embodiment shown in FIG. 3A, at least one electrode lead 341 and electrode are permanently attached to the sub-mandibular implant 200 at one of its corners. Another feedthrough lead 240 with a female implant connector 350 is available for attachment of another electrode lead 342 and electrode. The embodiment shown in FIG. 3A is typically used for unilateral implant patients, where a single electrode lead 341 is sufficient to achieve the desired clinical results, but would still allow a second electrode lead 342 and electrode to be added for bilateral applications. In the embodiment shown in FIG. 3C, the electrode leads 342 shown attach to the sub-mandibular implant 200 through implant connectors 350 only.

B. Implant Power Systems

Figure 4A:
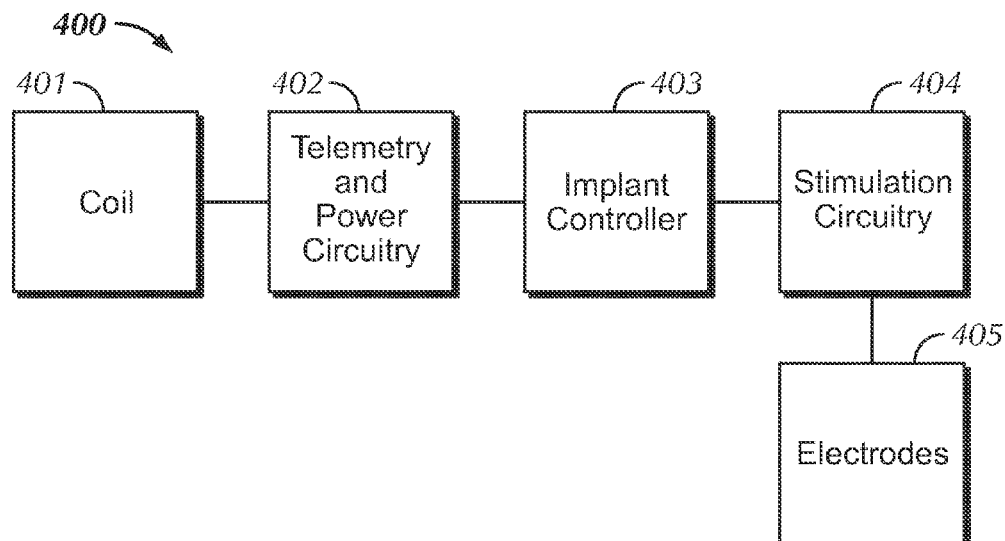
FIGS. 4A-4D show exemplary embodiments of IPG power systems.
Figure 4B:
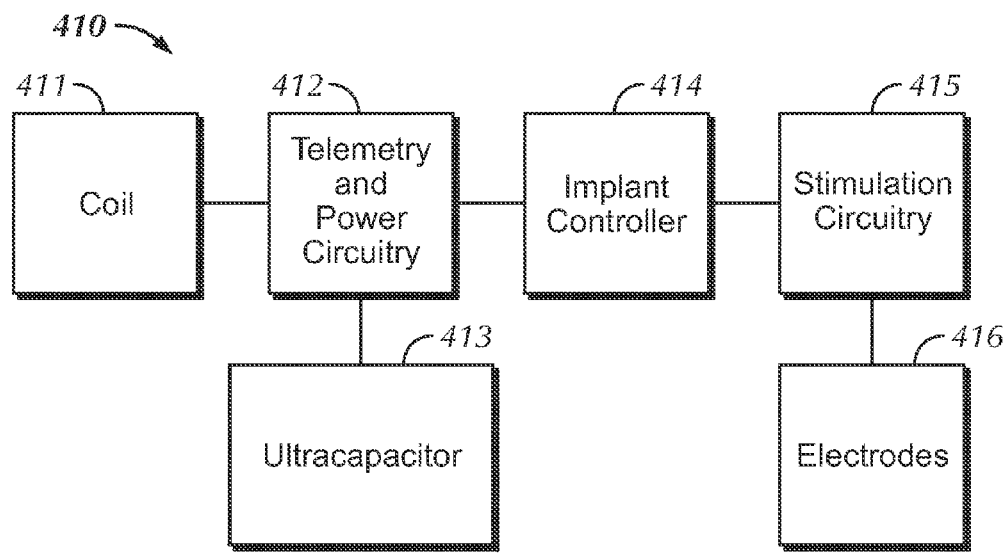
Figure 4C:
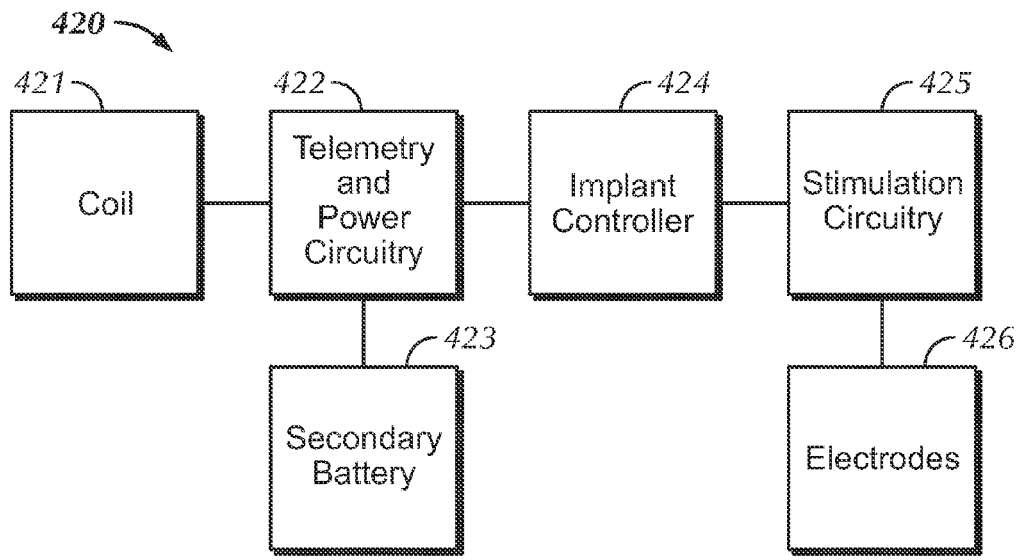
Figure 4D:
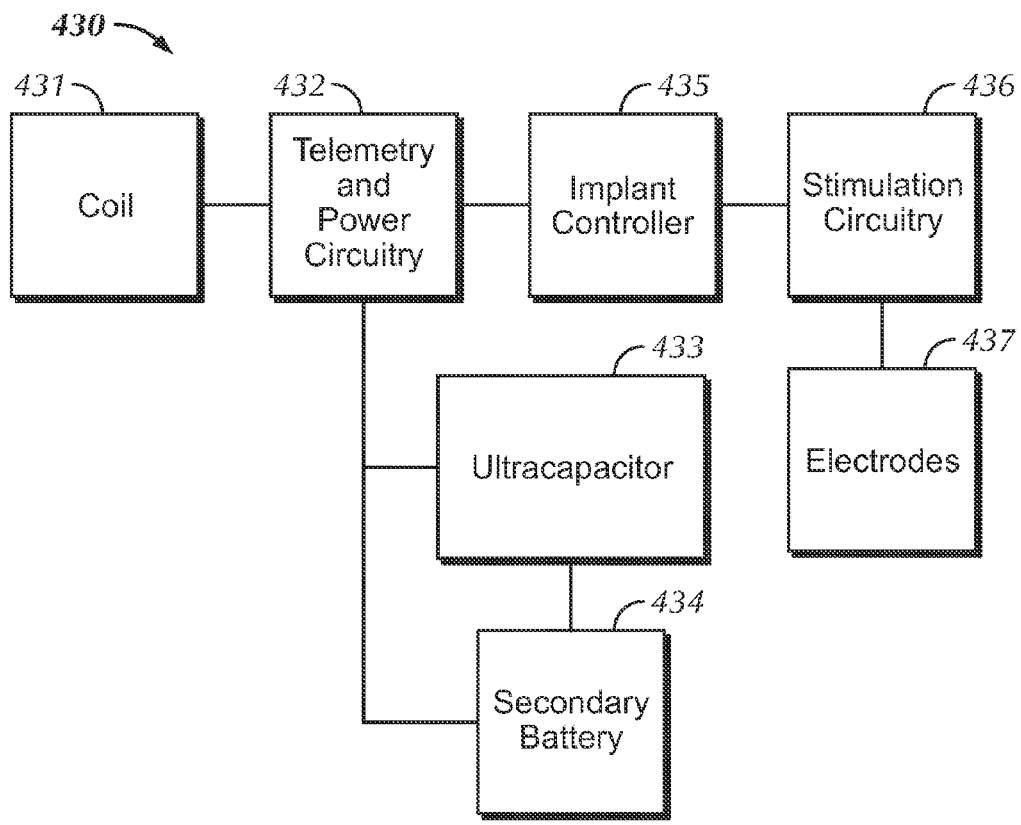

FIGS. 4A-4D illustrate exemplary embodiments of IPG power systems. Each embodiment illustrates a different power system. The four power systems are (1) RF-powered and controlled (FIG. 4A), with continuous application of RF power for operation of the implanted system; (2) ultracapacitor powered (FIG. 4B), with at least one short RF-powered charge period to supply sufficient power to the implant for operation for one sleep period; (3) secondary-battery-powered (FIG. 4C), with occasional RF-powered charging periods to supply sufficient power to the implant for operation for at least one sleep period a day for a week or more; and (4) a hybrid combination of ultracapacitor and secondary battery powered (FIG. 4D). In the absence of sufficient internal energy charge in the latter three embodiments, the system would allow operation to occur as in the first embodiment, that is, continuous application of RF power for the operation of the implanted system for the duration of the sleep period.

1. RF-Powered IPG Implant

FIG. 4A shows an exemplary embodiment of an RF-powered IPG implant 400. In the embodiment shown, the RF-powered IPG implant 400 has no internal power source. It receives power and commands, and exchanges data with an external controller via an inductively coupled RF power and data link. The link is a flat coil 401 attached via feedthrough pins to a coupling circuit 402 inside the IPG electronics enclosure. The coil 401 is AC coupled using one or more capacitors to prevent DC current leakage, which can damage tissue and cause failures in the hermetically sealed IPG feedthroughs.

The power and data signals are sinusoidal or similar waveforms at one or more frequencies that minimize energy losses but still support the bandwidth requirements for adequate data transfer rates. In certain embodiments, these signals are in the radio frequency (RF) range. In the embodiment shown, RF power and data are supplied externally with a matching coil, which may be held in position over the IPG coil 401 using a magnet, a strap, adhesive, or other method known to those skilled in the art. Limited coil misalignment is allowed and expected, including lateral displacement, vertical displacement, and out of plane angular displacement.

In other embodiments, the implant 400 operates according to the principle of RFID inductive coupling. The RF may be used to send power and/or control signals to the implant. In an embodiment, the implant 400 exploits the near-field characteristics of short wave carrier frequencies of approximately 13.56 MHz. This carrier frequency is further divided into at least one sub-carrier frequency. The sub-carrier frequency is obtained by the binary division of the carrier frequency. In certain embodiments, the implant 400 can use between 10 and 15 MHz. The implant 400 may further have two channels, Channel A and Channel B. Channel A is for power delivery and Channel B is for data and control.

In the embodiment shown in FIG. 4A, the received waveform is internally rectified and converted into one or more supply voltages within the RF-powered IPG implant 400 by coupling circuitry 402 and at least one circuit 404 used by the RF-powered IPG implant 400 in regular operations, including stimulation of the HGN. In certain exemplary embodiments, the circuit 440 may be an application specific integrated circuit (ASIC). The RF-powered IPG implant 400 uses its internal coil 401 to send a signal to the external devices, sometimes on a different carrier frequency, chosen to optimize its signal integrity and data transfer characteristics without interfering with the inbound signal transfer process. In certain embodiments, the RF-powered IPG implant 400 sends the signal from the internal coil 401 concurrently. The supply voltages are filtered and stored internally in capacitors. The capacitors are sized to power the RF-powered IPG implant 400 during temporary interruptions of the power link, but are not large enough to power the RF-powered IPG implant 400 for an entire sleep session.

2. Ultracapacitor-Powered IPG Implant

FIG. 4B shows an exemplary embodiment of an ultracapacitor-powered IPG implant 410. In the exemplary embodiment shown, the embodiment has the same elements described above, along with an ultracapacitor 413 that is large enough to store sufficient energy for a single sleep session, and receives power at very high rates with insignificant degradation of performance over time. In the ultracapacitor-powered IPG implant 410 embodiment, the external controller and associated coil are placed over the internal coil 411 just long enough to exchange data and charge up the ultracapacitor 413 power storage element. The rate at which the ultracapacitor 413 storage element charges is inversely related to the time required to bring it to full charge—the higher the charge rate, the shorter the charge time. Once the ultracapacitor 413 storage element is sufficiently charged, the patient may remove the external controller and external coil and begin a sleep session.

3. Secondary-Battery-Powered IPG Implant

FIG. 4C shows an exemplary embodiment of an IPG implant 420 with a secondary battery 423. The secondary-battery-powered IPG implant 420 is similar to the passive RF-powered IPG implant 400 (FIG. 4A), but with an internal battery 423 as a secondary source of power. The secondary battery 423 is large enough to store sufficient energy for at least a single sleep session and optimally for many more, and in certain embodiments is sufficient for at least a week of use. In this embodiment, the secondary-battery-powered IPG implant 420 receives its power for charging the secondary battery 423, receives commands, and exchanges data with an external controller using an inductively coupled RF power and data link. The external controller and its associated coil are placed over the internal coil 421 long enough to exchange data and charge up the secondary battery 423.

The rate at which the secondary battery 423 may be charged is typically longer than the charge times for ultracapacitor embodiments. Charge rates for secondary batteries such as lithium ion and lithium polymer are typically expressed as a percentage of charge capacity, typically from C/40 to C/1, where C is the charge capacity of the battery. For instance, a 200 milliamp-hour (mA-hr) battery could be charged at 50 mA for a C/4 rate. There is a trade-off for all battery chemistries in performance and longevity of the battery depending upon both the charge and discharge rates, as well as the depth of discharge prior to a charging session. High rates of charge and discharge are known to reduce the longevity of a secondary battery system, as well as deeply discharging a battery, whereas low rates of charge and discharge, and limited discharge durations with short periods of charge tend to enhance battery performance and longevity. This translates to a convenience factor for the patient in that to lengthen the time between surgical replacement for the IPG occurs the patient must frequently charge their implanted system, but if the patient desires to only charge when absolutely necessary it is more likely that the IPG will have a shorter implanted lifetime. These issues must be considered by the patient and the clinician as to how often and how long the device must be recharged.

4. Hybrid Powered IPG Implant

FIG. 4D shows an exemplary embodiment of hybrid-ultracapacitor and secondary-battery-powered IPG implant 430. In this embodiment, the hybrid-ultracapacitor and secondary-battery-powered IPG implant 430 receives power for charging the internal ultracapacitor 433 and its secondary battery 434, receives commands, and exchanges data with an external controller with an inductively coupled RF power and data link. Charge may be stored in the secondary battery 434, allowing sleep sessions with no external hardware for up to a week at a time (except for initial IPG turn-on and final turn-off). The patient may also charge for just a few moments to fill the ultracapacitor 433, or use the hybrid-ultracapacitor and secondary-battery-powered IPG implant 430 in only a fall-back operation of ultracapacitor operation only when the service life of the secondary battery 434 is exhausted, avoiding the need for surgical replacement.

Other forms of implanted power sources may also be used without departing from the scope of this invention, such as harvesters of kinetic energy, fuel cells, and even atomic sources.

C. Exemplary IPG Accessories

Figure 5C:
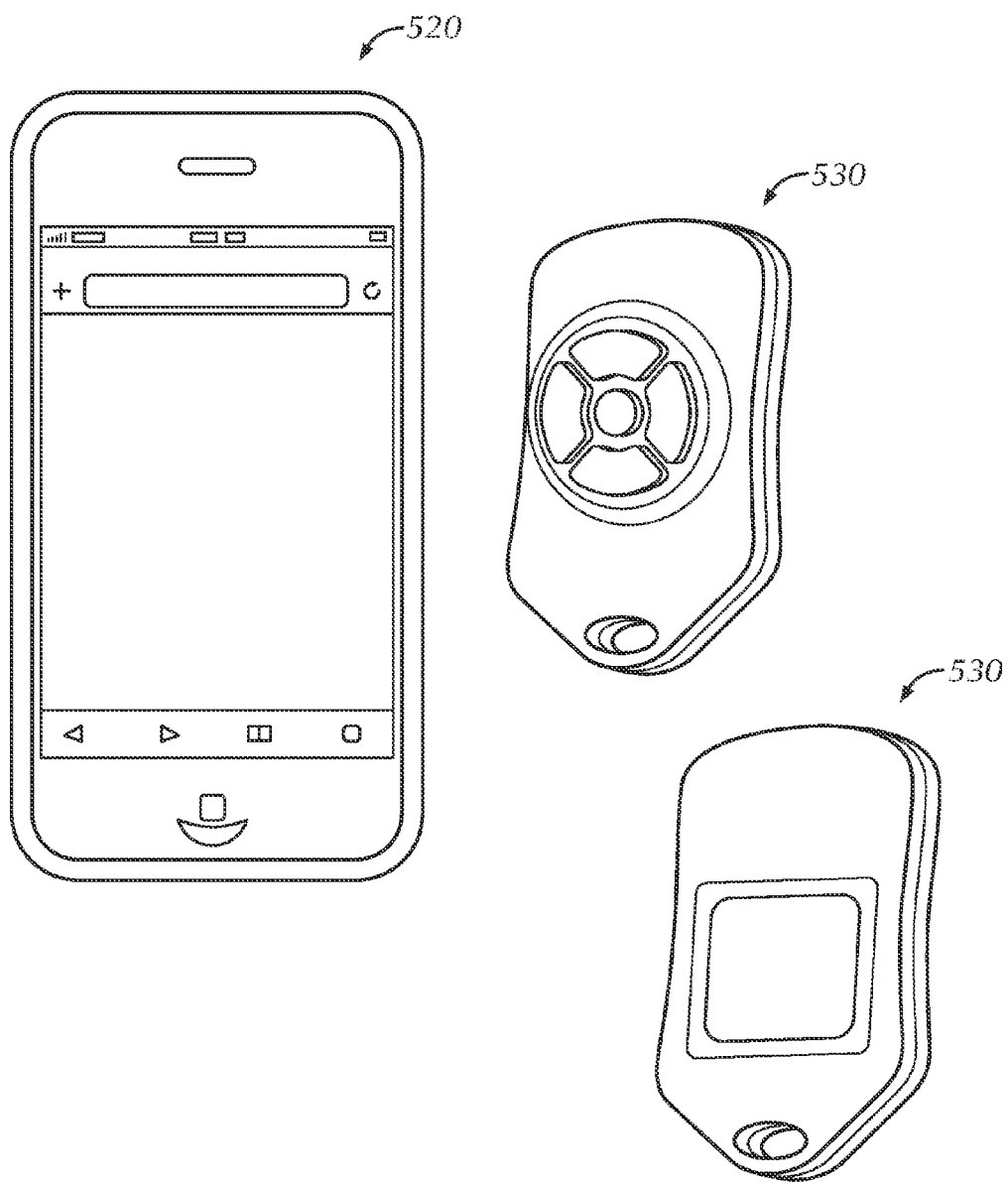

In certain embodiments, the IPG interfaces with other devices. FIGS. 5A-5D show exemplary embodiments of IPG accessories. The other devices may include, for example: (1) an external controller with an integrated or attached coil (FIGS. 5A and 5B); (2) a charging station to replenish energy to the external controller (FIG. 5D); and (3) a remote control that communicates with the controller (FIG. 5C). In certain embodiments, the remote control also establishes the operating mode for the patient and/or monitors the performance of the implant and controller. These embodiments are described below.

1. External Controller

FIG. 5A shows an exemplary embodiment of an external controller 500. In this embodiment, the external controller 500 has a rechargeable power source such as a secondary battery system (lithium ion, etc.), electronics to power and communicate with the IPG, and a telemetry portion that communicates with the remote control. The telemetry portion as shown is a coil, but can be any item used by those skilled in the art to transmit and receive data. In the embodiment shown the coil as shown is integrated with the external controller 500, but can be separate from the external controller 500 in other embodiments. In the embodiment shown, the telemetry portion between the external controller 500 and the remote control (FIG. 5C) uses Bluetooth or other wireless communication standard. Utilizing such a standard allows commonly available technologies to be utilized for the remote control and additionally allows communication with a computer programming system. The embodiment shown is exemplary only, and not limited to what is shown. In other embodiments, the external controller 500 communicates with the remote control or clinician's programmer (such as a computer or other electronic device) using a cable having a USB or other connection known to those skilled in the art. The cable can be in addition to or in place of the wireless telemetry.

The external controller 500 has user interface functions with an activity indicator, such as, for example, an LED indicating whether the device is operational. The interface may also have another indicator showing link and activity with the remote control. The external controller 500 interfaces with a recharging station (FIG. 5D), so that when the patient starts or ends a sleep session the controller 500 may be easily removed from or returned to the recharging station.

In the exemplary embodiment shown in FIG. 5A, the external controller 500 is mounted to a collar or neck strap 501 that allows simple fitting of the external controller 500 about the patient's neck and provides optimal alignment with the sub-mandibular IPG implant 200 (FIGS. 2A-2D) for proper power and data transfer. The neck and sub-mandibular location of the external controller 500 and sub-mandibular IPG implant 200 are minimally affected by head and neck movement during sleep, with typical patient movement during sleep resulting in only minimal forces applied to the devices.

FIG. 5B shows another exemplary embodiment of an external controller 510. In this exemplary embodiment, the controller 510 is worn behind the ear (BTE) and is similar in shape to a speech processor used with a cochlear implant. This shape gives the BTE controller 510 a low profile, which helps keep it from being dislodged during sleep. This shape is exemplary only, and not limited to what is shown. The controller operatively connects to a coil, which is placed near the mastoid bone implant 100 (FIGS. 1A-1F) prior to sleeping. The controller coil optionally has a magnet to help align it with the internal coil 120.

The BTE controller 510 has user interface functions with an activity indicator, such as, for example, a charge indicator LED 512 indicating whether the device is operational. The interface may also have another telemetry indicator LED 513 showing link and activity with the remote control. The BTE controller 510 interfaces with a recharging station (FIG. 5D), so that when the patient starts or ends a sleep session the BTE controller 510 may be easily removed from or returned to the recharging station.

2. Remote Control

FIG. 5C shows an exemplary embodiment of a remote control 530. In the embodiment shown, the remote control 530 provides the patient with a simple and intuitive interface to the IPG system. The remote control 530 allows the patient to start and stop IPG operation, and interrogate the IPG system and external controller 500 (FIG. 5A) for proper function, status of the communication and power link to the IPG, and status of external controller 500 power. With the embodiment of the remote control 530 shown, the patient may also choose operating modes for the IPG, including but not limited to standard sleep mode, exercise mode, and alternative operating modes. If enabled by the clinician, the remote control 530 also allows the patient to adjust stimulation levels. The embodiment is exemplary only, and not limited to what is shown. For example, the remote control 530 may communicate with the external controller 500 using a cable having a USB or other connection known to those skilled in the art. The cable can be in addition to or in place of the wireless telemetry.

In certain embodiments, the remote control is incorporated into an Apple iPhone™ 520 or other wireless device. The iPhone™ 520 has an excellent user interface, Bluetooth telemetry capability, and is supported as a development platform for commercial applications. The iPhone™ 520 also allows the patient to transfer data to and from the Internet, enabling secure communications to the clinician and the manufacturer. Using a commercially available remote control also eliminates the need to manufacture the remote, simplifying the supply, support, and (potentially) the patient learning curve. Using a commercially available alternative also provides the opportunity to provide extensive help resources, such as context sensitive help screens, training videos, and live help from company and clinician support centers if required by the patient. In certain embodiments, one or more of the iPhone™ 520 commercial functions are disabled, with the iPhone™ 520 only acting as a remote control for the external controller 500/IPG system. The iPhone™ 520 would enable the patient to operate the implant system and have access to help documents and videos that help the patient use the system. In other embodiments, one or more of the iPhone™ 520 commercial functions are enabled. Other embodiments of the iPhone™ 520, or other forms of smart phones may also be used, and may be more readily available in certain markets around the world.

In certain embodiments, the external controller 500 interfaces with a computer. The interface may be wireless, or by a cable having a USB or other connection known to those skilled in the art. The cable can be in addition to or in place of the wireless telemetry. The computer may be a Windows™, UNIX™, Linux™ or Macintosh™ based notebook or desktop computer having Bluetooth communication capability. Other telemetry known to those skilled in the art may also be utilized. Using telemetry known to those skilled in the art facilitates compatibility with industry standards and systems. Other wireless communication standards may be used without departing from the scope of the invention. The computer maintains a database to store all pertinent patient data, including stimulation settings, follow-up session changes, etc. The computer may also have an application with an intuitive method to test and program the IPG system so that the clinician can set IPG implant stimulation parameters for some or all of its operating modes.

3. Recharging Station

Figure 5D:
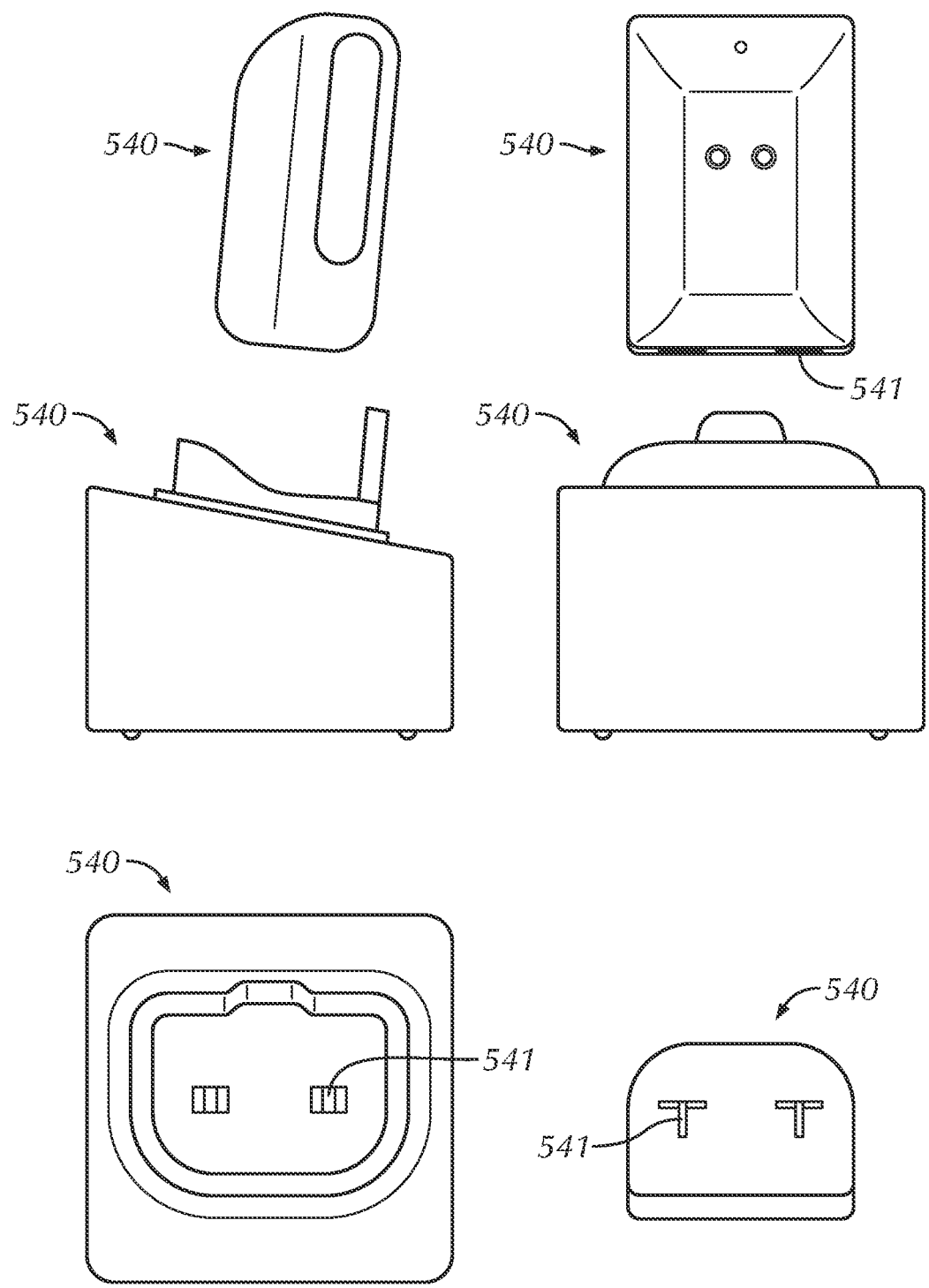

FIG. 5D shows an exemplary embodiment of a recharging station 540. In the embodiment shown, the recharging station 540 is a cradle-like device powered by a wall-wort power supply. The external controller 500 (FIG. 5A) is placed in its cradle for recharging during non-sleep periods. Recharging may be inductive, relying upon the orientation of the external controller 500 within the cradle for inductive coupling to the mating coils of the devices. Recharging may also utilize metal contacts 541 on the exterior surface of the controller for direct recharging to the external controller 500, much like that of a standard cordless telephone handset. In certain embodiments, the wall-wort power supply is a commercially available recharger.

II. Electrodes

The IPG system delivers stimulation to targeted nerves or nerve fibers using implanted electrodes. In certain embodiments, the electrodes consist of biocompatible silicone rubber with a Dacron or similar woven material to lend tear resistance to the design. The electrode contacts are fabricated with 90 percent platinum and 10 percent iridium (90/10 Pt—Ir), known in the industry as highly biocompatible materials with excellent properties for neural excitation. Other materials known to those skilled in the art may also be used.

Researchers treating obstructive sleep apnea have discovered that the muscles of interest are activated by HGN nerve fibers lying interior to the HGN with respect to the outside of the patient (i.e., the dorsal aspect of the HGN). FIGS. 6A-6G (discussed below) show exemplary embodiments of IPG electrodes that take advantage of this neural organization. For example, in certain embodiments one or more electrode contacts lie preferentially on the inside surface of the cuff or trough on the interior portion. Some embodiments have at least four contacts, others as many as eight, which act as excitatory electrode contacts. Other embodiments have additional contacts located longitudinally distal to the excitatory contacts. In these exemplary embodiments, the additional contacts have a common electrical connection to the IPG case, or are multiplexed to at least one IPG output. This provides many ways of stimulating the HGN nerves, including contact to case indifferent, contact to array indifferent, contact to contact (bipolar or multipolar), and any combination of the above. These and other exemplary electrode embodiments are discussed below.

A. Electrode Designs

Electrodes can be designed in many different ways. Three possible designs include the fully encircling cuff (FIGS. 6A-6D), the helical cuff (FIG. 6E), and the open trough (FIGS. 6F-6G). Embodiments of each are discussed below. These embodiments are exemplary only, and not limited to what is shown.

1. Fully-Encircling Cuff Electrodes

Figure 6A:
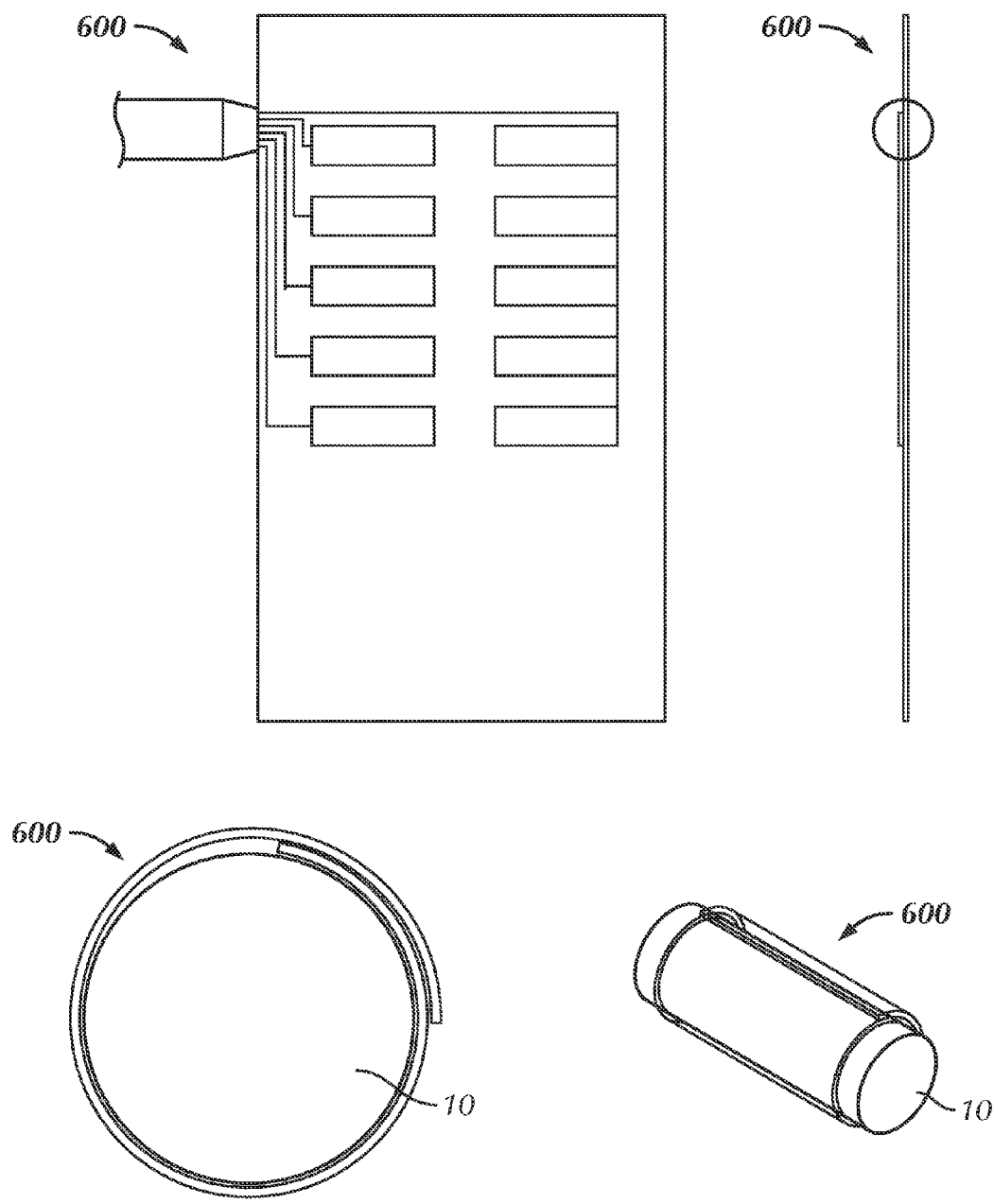
FIGS. 6A-6G show exemplary embodiments of IPG electrodes.

FIGS. 6A-6D show exemplary embodiments of fully encircling cuff electrodes 600. For example, FIG. 6A shows a non-perforated fully encircling cuff. Non-perforated fully encircling cuffs must be used with care, as connective tissue buildup in response to a foreign body can cause an increase of HGN 10 diameter and potential constriction of the HGN 10 after surgery. Some swelling of the HGN 10 is expected due to the surgical trauma the nerve endures when it is dissected and the electrode is installed. The swelling and increase in connective material may damage the nerve, due to the effect of pressure on the blood supply of the nerve trunk, and the increased pressure on the nerve axons of the trunk.

Figure 6B:
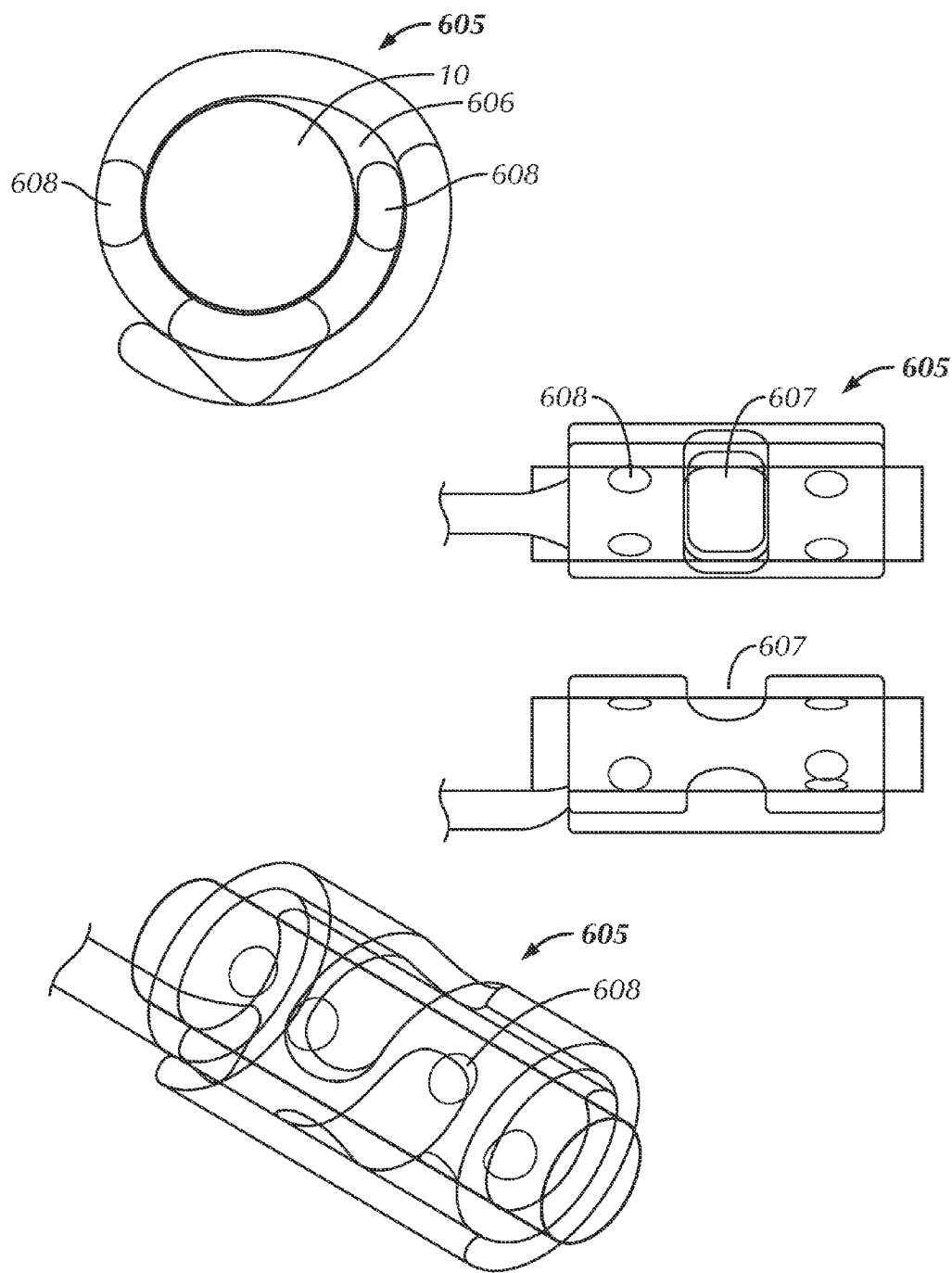
Figure 6C:
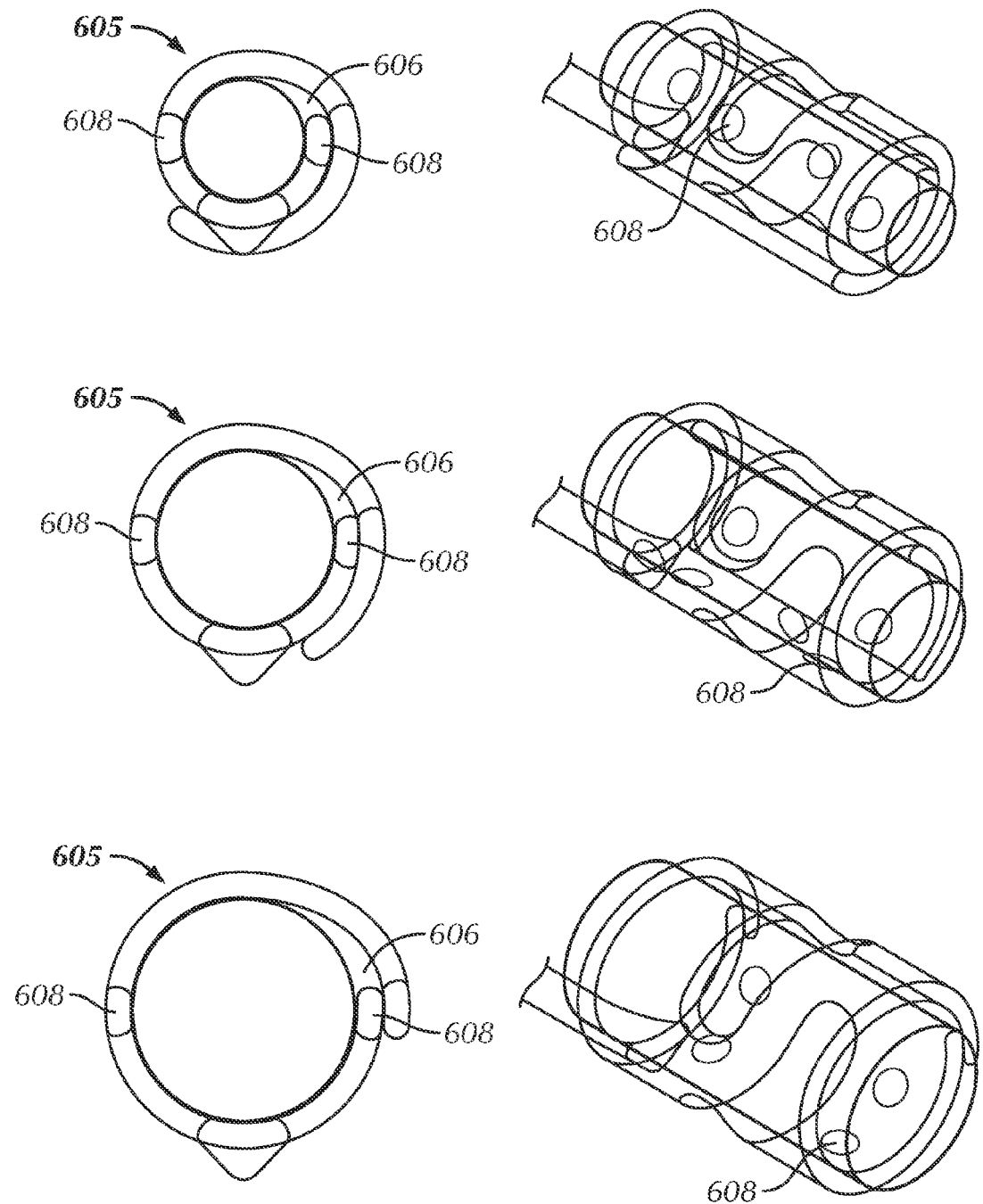
Figure 6D:
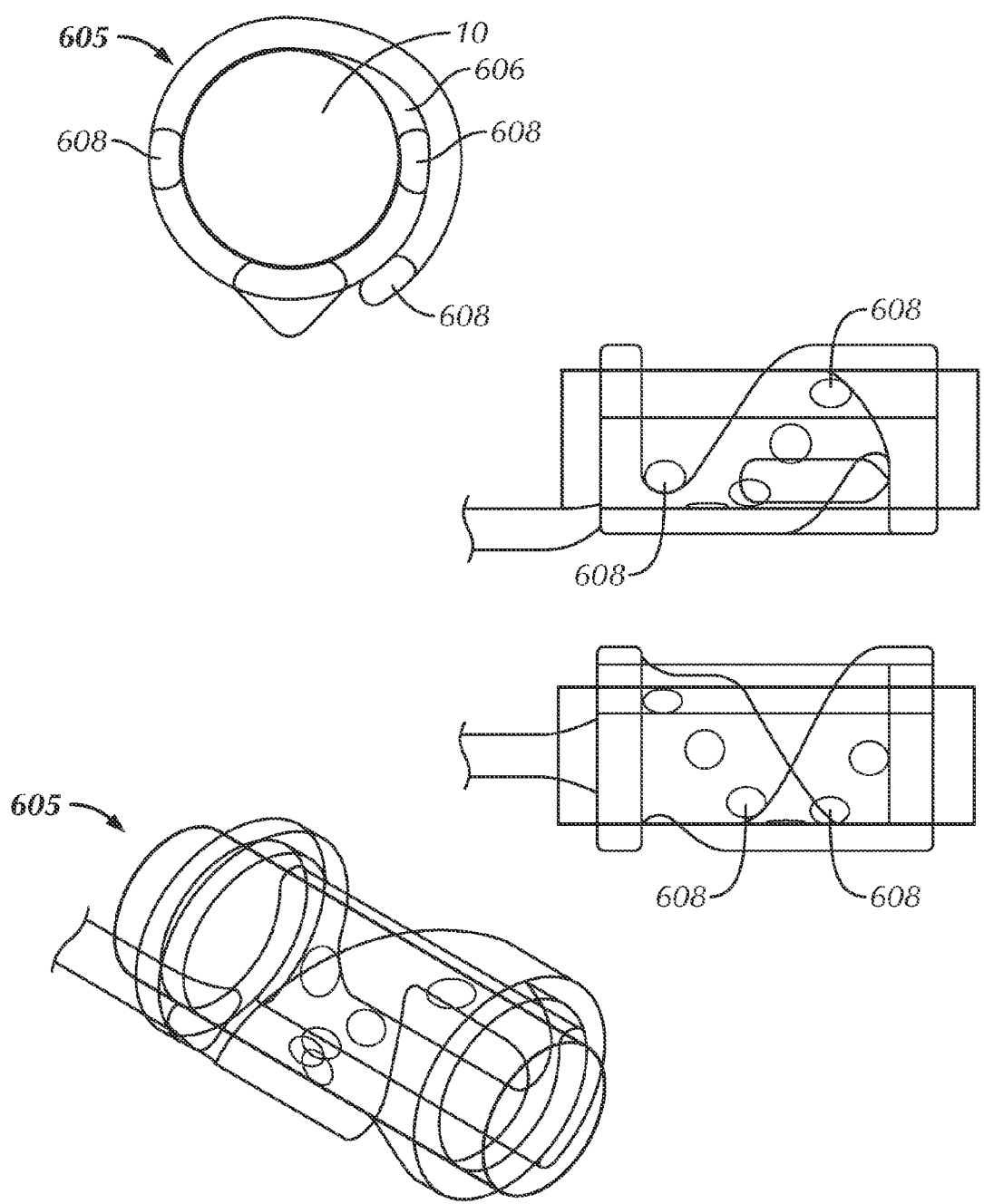

In other embodiments, the implantable neurostimulator system of the present invention includes a fully encircling perforated cuff electrode 605 (FIGS. 6B-6D). In some embodiments, the perforated cuff electrode 605 is from about 4 mm to about 12 mm in diameter. In some embodiments, the perforated cuff electrode 605 is from about 6 mm to about 10 mm in diameter. In yet another embodiment, the perforated cuff electrode 605 is about 8 mm in diameter.

Alternatively, the diameter of the perforated cuff electrode 605 is expandable and increases or decreases in accordance with the diameter of the HGN 10. In further embodiments, the perforations 607 and/or the plasticity of the material comprising the perforated cuff electrode 605 allows accommodation of the expected change in diameter and swelling response and prevents ischemic constriction of the HGN 10. In some embodiments, the perforations 607 are about 2 mm in diameter. The perforated cuff electrode 605 may also be self-sizing. In some embodiments, the fully encircling perforated cuff electrode does not physically contact the entire circumference of the HGN 10. In still other embodiments, the perforated cuff electrode 605 overlaps upon itself, thereby creating an empty space 606 into which a nerve may expand without ischemic constriction. In certain expandable cuff embodiments, the electrode diameter is expandable, with ranges extending from a diameter of approximately 2 mm to a diameter of approximately 12 mm. Other expansion ranges may be used without departing from the scope of the invention.

In some embodiments, the perforated cuff electrode 605 includes electrical contacts 608 on its inner surface facing a nerve. The perforated cuff electrode 605 may include any number and/or arrangement of contacts 608. For example, the perforated cuff electrode 605 can include at least six contacts 608. In other embodiments, the perforated cuff electrode 605 includes at least eight contacts 608. In certain embodiments, the contacts 608 are axially aligned relative to the perforations 607 of the perforated cuff electrode 605 (FIG. 6B).

Alternatively, the contacts 608 can be axially staggered relative to the perforations 607 (FIGS. 6C-6D). In some embodiments, the contacts 608 are about 1 mm in diameter. In still other embodiments, the distance between contacts 608 is about 1 mm. The contacts 608 need not circumscribe the entire circumference of the nerve. In certain embodiments, the flap of the electrode cuff overlaps an electrode lead (FIGS. 6B-6C) and in others it does not (FIG. 6D). In further embodiments, the positions of the contacts 608 relative to a nerve changes as the diameter of the nerve increases or decreases. The contact size, number, location, and arrangement are exemplary only, and not limited to what is shown. Other combinations may be used without departing from the scope of the invention.

2. Helical Cuff Electrodes

Figure 6E:
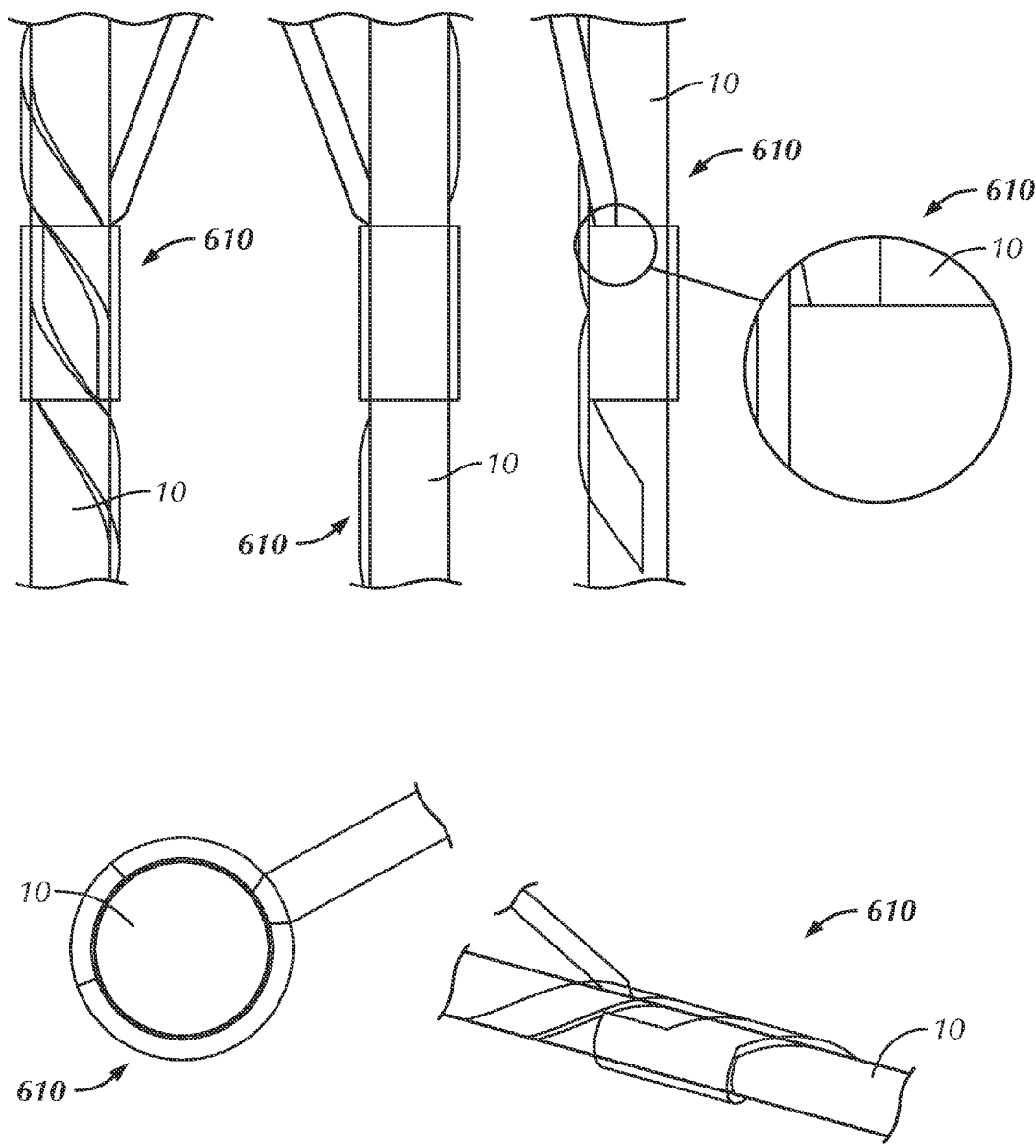
Figure 6F:
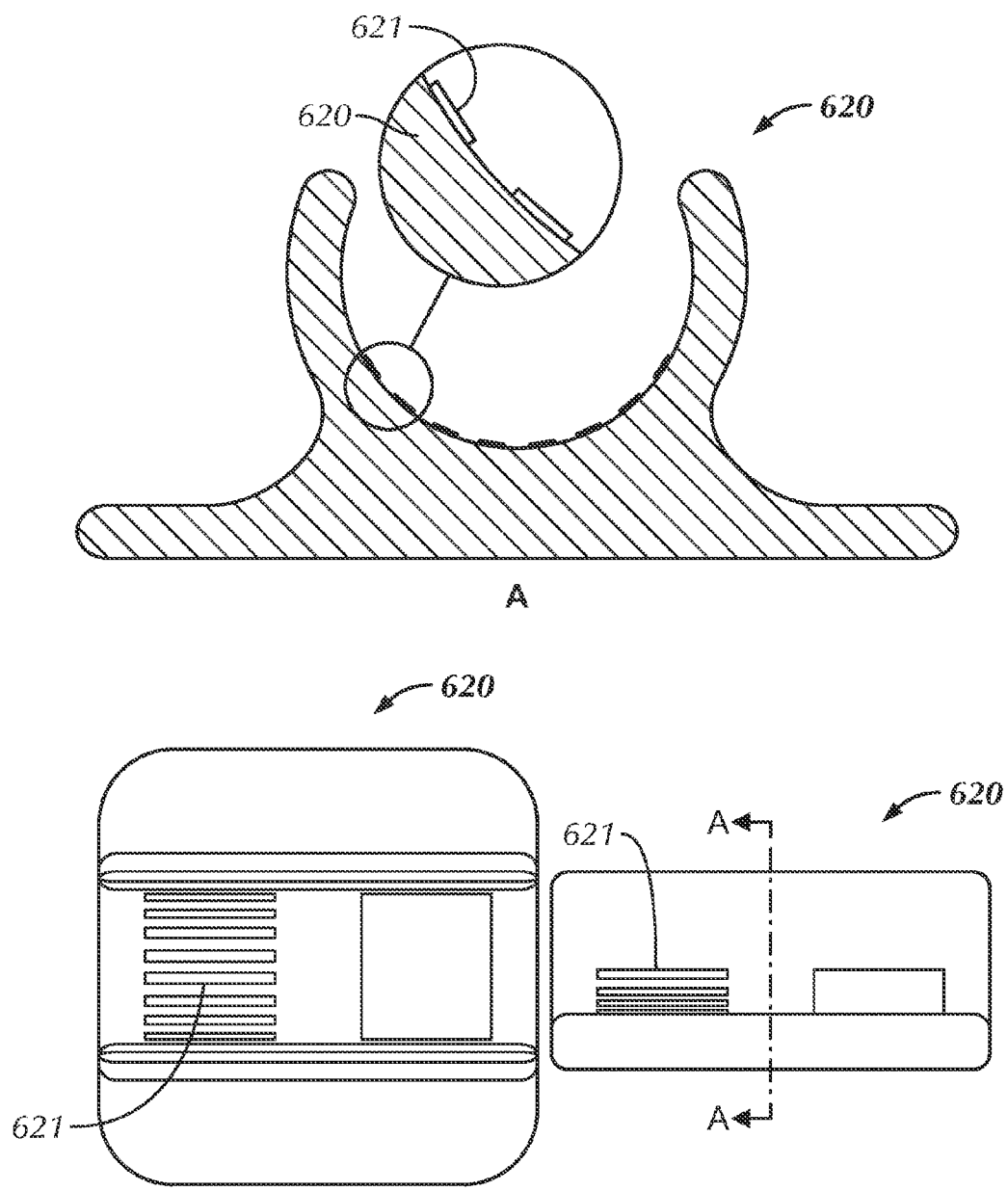
Figure 6G:
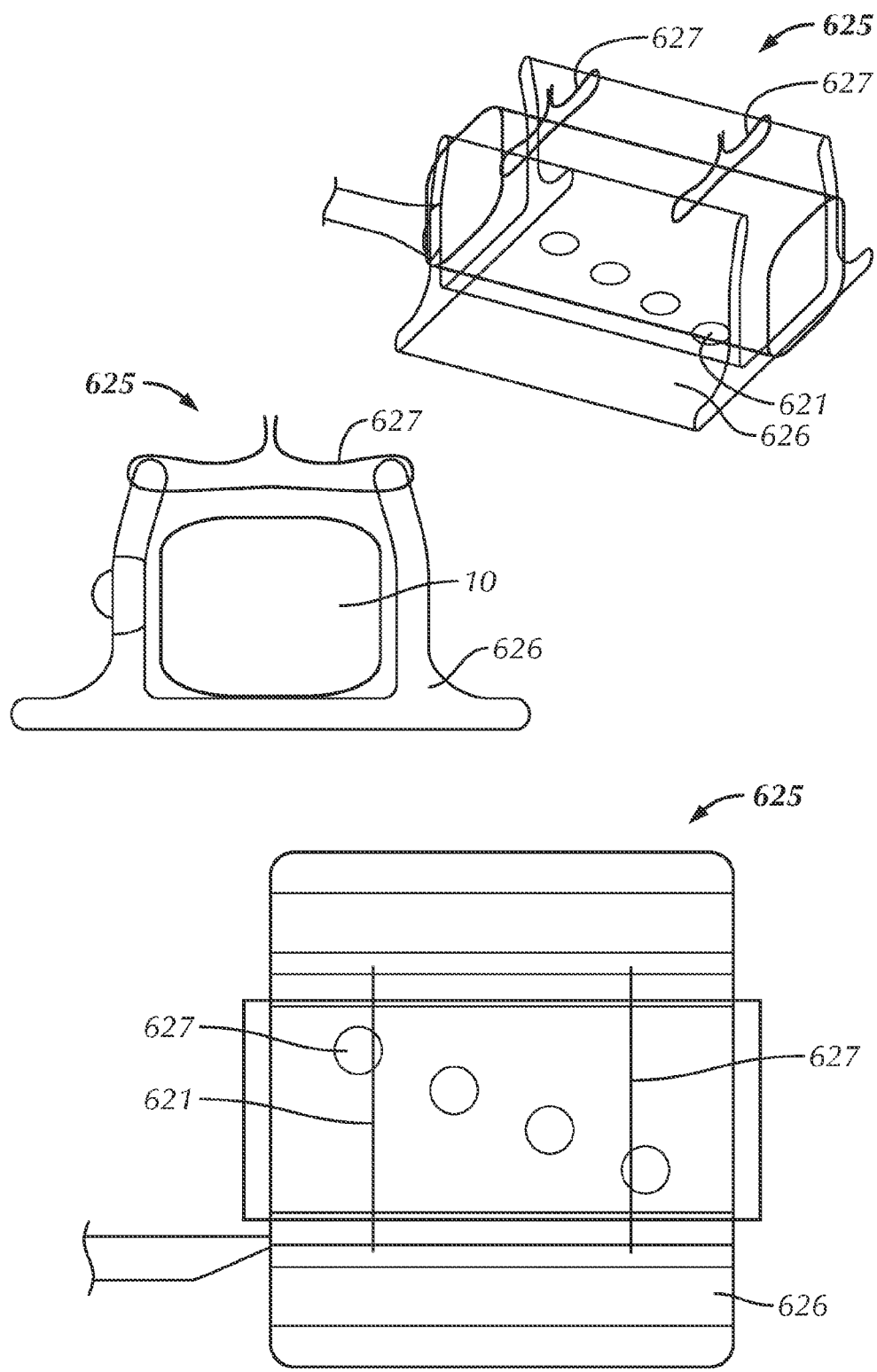

FIG. 6E shows an exemplary embodiment of a helical cuff electrode 610. The helical cuff electrode 610 mitigates the problems of a fully encircling cuff electrode 600 (FIG. 6A). One example is a helical cuff electrode developed by the Huntington Medical Research Institute for stimulating the vagus nerve. In this example, the cuff electrode 610 winds around a nerve trunk, but does not overlap itself and is not sutured into a fixed diameter. In still other exemplary embodiments, the cuff electrode 610 is self-sizing. A self-sizing cuff encircles the nerve in its natural state. The cuff electrode 610 overlaps its ends but still allows some expansion of the cuff until the connective tissue overgrowth assumes its final state after surgical implantation.

3. Open Trough Electrodes

FIG. 6F shows an exemplary embodiment of a round-bottomed open trough electrode 620. In the exemplary embodiment shown, the contacts 621 reside on the inside of the trough. In certain round-bottomed open trough embodiments, contacts 621 are present on the innermost region of the interior of the trough, while the portion of the trough that covers the outer portion of the HGN 10 has no contacts.

The open trough electrode 620 addresses some of the problems associated with the fully encircling electrode 600 design by lying underneath the nerve trunk, rather than completely encircling or enclosing the nerve trunk. This allows tissue expansion and swelling, as well as the connective tissue buildup, while still allowing the nerve to expand away from the trough without constriction. The exemplary open trough electrode 620 embodiment shown slips underneath the HGN 10 with little dissection. The normal forces holding the tissues of the neck in place help keep the HGN 10 aligned with the open trough electrode 620. The open trough electrode 620 may optionally be anchored to surrounding tissue to maintain its position with respect to the HGN 10 to prevent distension or other loading forces upon the HGN 10.

In some embodiments of the present invention, it is desirable to place the contacts 621 of an open trough electrode 620 preferentially against one surface of the nerve bundle, and it is also desirable to avoid placing any forces against the nerve as it lies in the electrode 620 to force it into a new or different shape from its native shape. In some embodiments, the open trough electrode 620 maintains the position of the nerve within the electrode trough up until the point at which connective tissue growth has secured the nerve and electrode 620 interface.

FIG. 6G shows a flat-bottomed variant 625 of an open trough electrode. While the contemporary textbook view of the shape of peripheral nerves is that of rounded structures, they may in fact also assume oval or flattened shapes depending upon their internal structure and where they lie in respect to other tissue structures such as muscles, bones, and fascial planes. One of the internal structure determinants of cross-sectional shape may be the absence or presence of fascicular organization. The design of a flat-bottomed open trough electrode 625 advantageously allows a flattened nerve to lie against a series of contacts on a flattened surface, thereby also allowing a lower profile between the tissue structures where the peripheral nerve occurs.

In some embodiments of the present invention, an implantable neurostimulator system includes at least one flat-bottomed open trough electrode 625. In some embodiments, an absorbable suture material 627 is placed between the flaps 626 of the electrode 625 to prevent the nerve from moving out of the trough during the connective tissue growth period after initial implantation. In some embodiments, the suture material 627 has a finite lifetime before dissolving. This limits the potential for long-term damage that might result from a permanent compressive or retentive mechanism such as a hard flap or fixed diameter cuff. In some embodiments, the flat-bottomed open trough electrode 625 provides a means of selective activation that only temporarily constrains the nerve within the electrode, and presents a lower profile for the same cross sectional nerve area than a comparable rounded trough electrode.

B. Electrode Configurations

The fully encircling cuff, helical cuff, and open trough electrodes can be configured as monopolar, bipolar or multipolar electrodes. For example, electrodes may be composed of at least one pair of platinum/iridium cathode and anode contacts arranged in a helical pattern on a substrate of heat shaped, biocompatible polystyrene strip material. The contact pairs are oriented transversely to the HGN to drive stimulus into internal nerve fibers. In another embodiment the electrode design is a helix. In another embodiment, the electrode design is a cuff with fingers, and in another embodiment, the electrode design is an electrode that penetrates the nerve itself. FIGS. 7A-9B show selected exemplary embodiments of these electrode configurations. The number and arrangement of the contacts shown in each of these figures are exemplary only, and not limited to what is shown.

1. Monopole Electrode Configuration

Figure 7A:
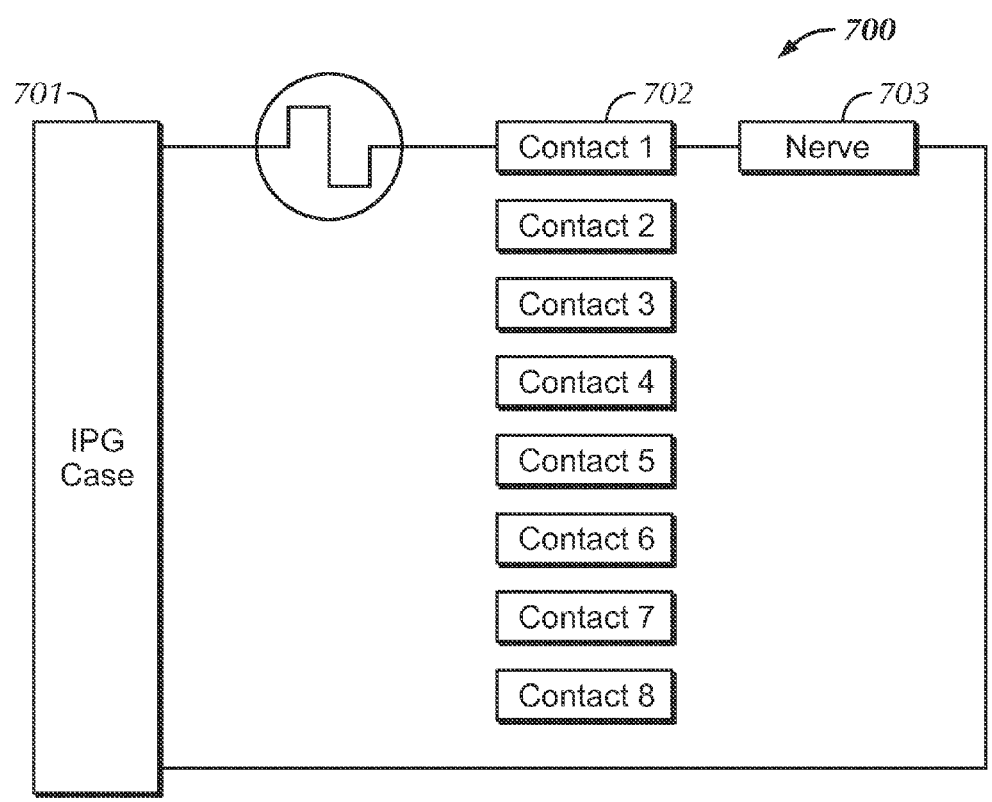
FIGS. 7A and 7B show exemplary embodiments of monopole electrode configurations.
Figure 7B:
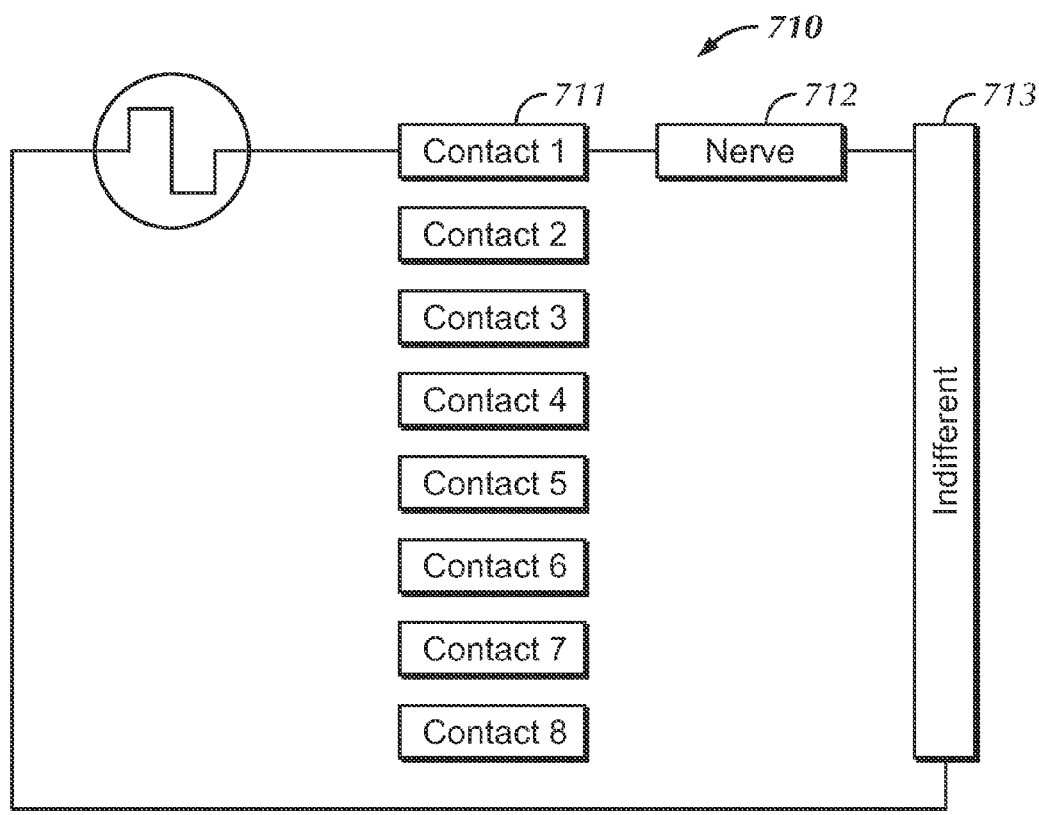

FIGS. 7A and 7B show exemplary embodiments of monopole electrode configurations. Monopolar stimulation typically results in lowered stimulation thresholds since there is no shunting of current between contacts before it is free to enter the nerve bundle. FIG. 7A shows an exemplary embodiment of a monopolar, single cathodal contact, IPG case return electrode 700. In the configuration shown, a stimulation electrode contact 702 acts as the excitatory cathodic contact, with the IPG case 701 providing the complementary current return path. FIG. 7B shows an exemplary embodiment of a monopolar, single cathodal contact, indifferent array return electrode 710. In the embodiment shown in FIG. 7B, a stimulation electrode contact 711 acts as the excitatory cathodic contact, with another array of contacts (an indifferent array) 713 furnishing the complementary current return. The indifferent array 713 has one or more contacts, with the indifferent array contacts 713 typically having a larger surface area than the excitatory contact.

In monopolar or bipolar stimulation, the waveform is often asymmetrical biphasic, since it is sometimes undesirable to have a final excitatory phase of cathodic stimulation on the case electrode. Those skilled in the art of electrical stimulation understand that symmetrical biphasic pulses may result in excitatory cathodic phases of stimulation at each of the necessary contacts of a stimulation electrode. By utilizing asymmetrical waveforms the first cathodic phase is of an amplitude and phase duration adequate to achieve excitation of the nerve, but the later anodic phase is both longer and of lower amplitude, which at the return or second electrode contact, results in a cathodic phase which is not of sufficient amplitude to cause nerve excitation. The common practice of using a large indifferent or case electrode at a location away from the nerve electrode acts to reduce current density at the indifferent electrode at a site away from the nerve, which also minimizes the likelihood of excitation at that electrode.

2. Bipolar Electrode Configuration

Figure 8:
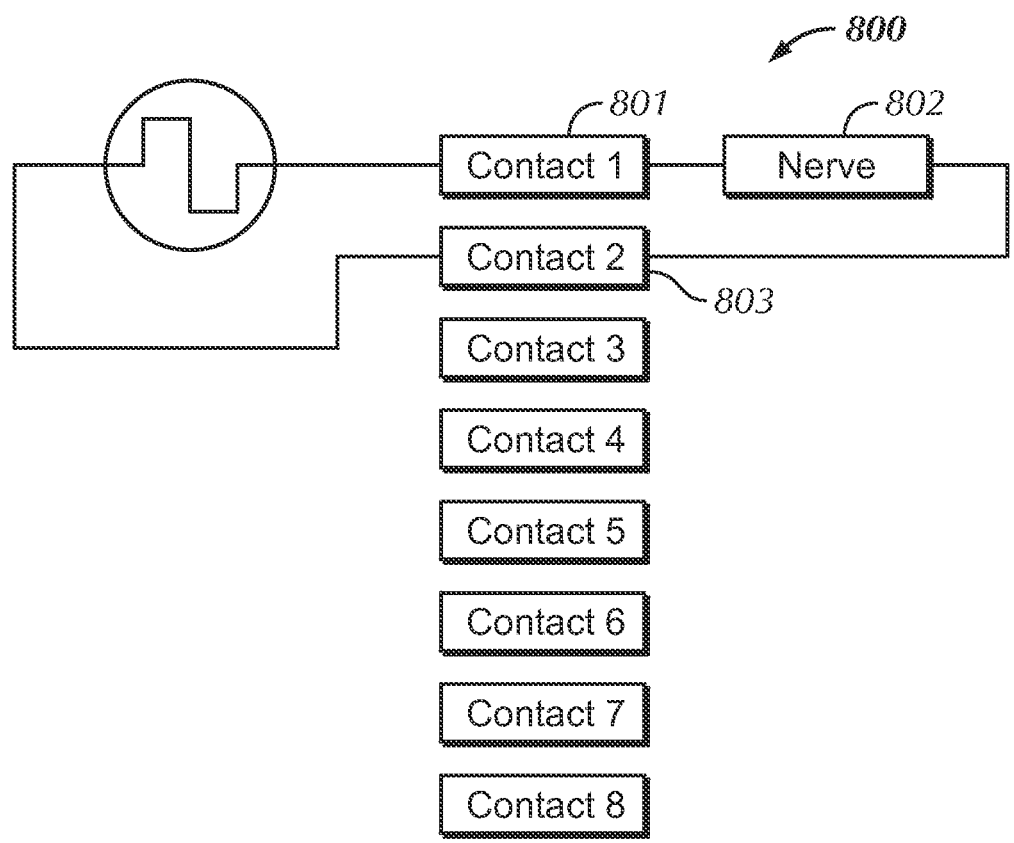
FIG. 8 shows an exemplary embodiment of a bipolar electrode configuration.

FIG. 8 shows an exemplary embodiment of a bipolar electrode configuration 800. Bipolar electrode configurations 800 have two contacts with approximately the same geometric surface area stimulating as a pair. One electrode is the excitatory contact 801 and the other electrode is the return (indifferent) contact 803. The charge delivered and recovered by both contacts is approximately equal. Therefore, the return (indifferent) contact 803 can cause nerve 802 excitation during the last phase of the waveform if the waveform is symmetrical, and can cause anodic phase excitation depending upon the orientation and other features of the nerve 802 within the vicinity of the second contact 803. If the waveform utilized in bipolar stimulation is symmetrical then it is likely that excitation will occur at each electrode contact. If the waveform is asymmetrical, it is likely that excitation will only occur at the primary cathodic contact 801.

3. Multipolar Electrode Configuration

Figure 9A:
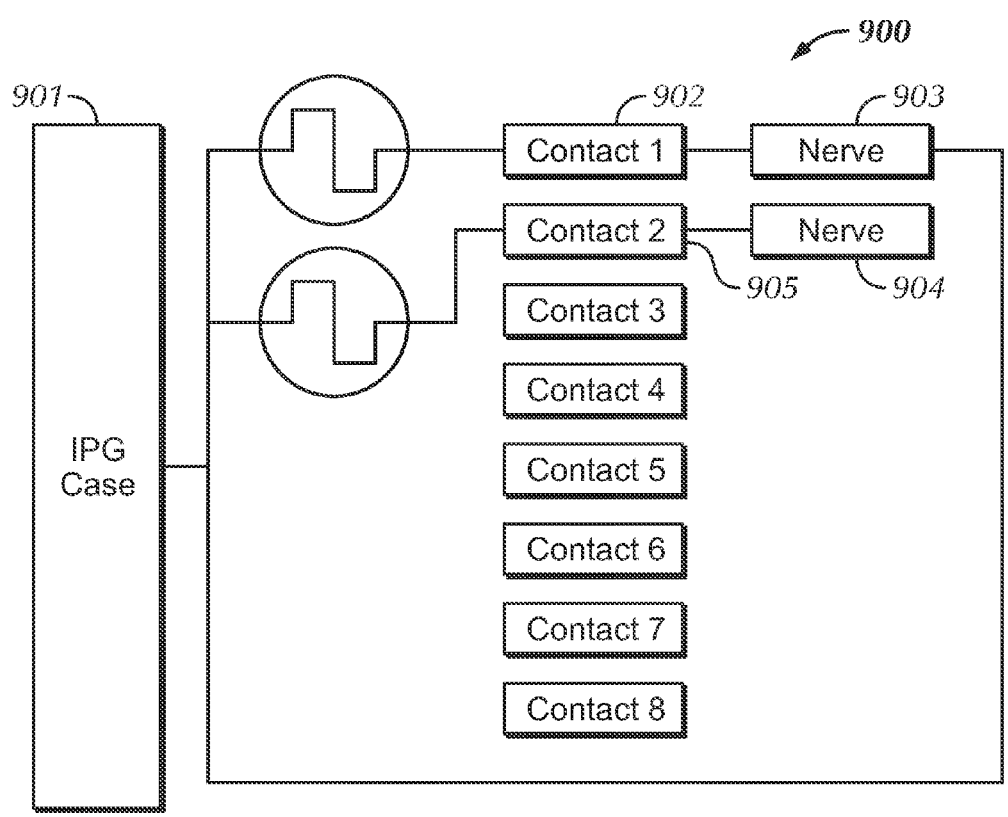
FIGS. 9A and 9B show exemplary embodiments of multipolar electrode configurations.
Figure 9B:
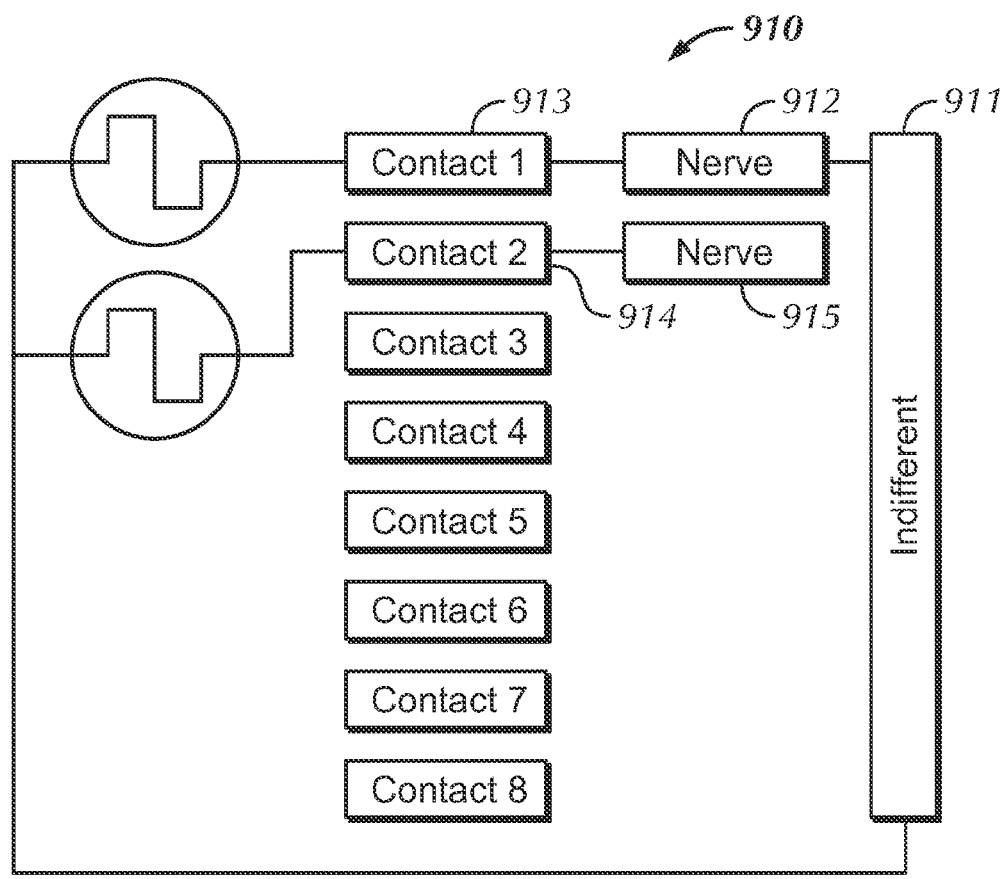

Multipolar configurations allocate three or more contacts to stimulate as an array. FIGS. 9A and 9B show exemplary embodiments of multipolar electrode configurations. FIG. 9A shows an exemplary embodiment of a multipolar, two cathodal contact, IPG case return multipolar electrode array 900. The cathodal contacts 902, 905 typically function as the excitatory contacts. Although only two cathodal contacts 902, 905 are shown, each with their own source, additional cathodal contacts (with either independent or shared sources), may be used without departing from the scope of the invention. In the embodiment shown, the IPG case 901 provides the complementary current return. This embodiment is exemplary only, and not limited to what is shown.

FIG. 9B shows an exemplary embodiment of a multipolar, two cathodal contact, indifferent contact return multipolar electrode array 910. The cathodal contacts 913, 914 typically function as the excitatory contacts. Although only two cathodal contacts 913, 914 are shown, each with their own source, additional cathodal contacts (with either independent or shared sources), may be used without departing from the scope of the invention. In the embodiment shown, another array of contacts (the indifferent array) 911 provides the complementary current return. This embodiment is exemplary only, and not limited to what is shown.

In multipolar configurations, current fields may be manipulated in different or multiple directions, thereby changing neural recruitment patterns, and may do so without adversely spilling over or recruiting undesired neural populations. This mode of operation is best served by current sources for each electrode contact that can be activated concurrently, i.e., by a single timing generator. Alternatively, multiple timing generators may be used with multiple contacts to recruit different populations of neurons offset in time that result in approximately simultaneous activation of the motor units with which they associate. This occurs because of the relatively long time constant of muscle activation with respect to motor nerve recruitment but is not to be confused with concurrent stimulation as described previously, which can result in neural recruitment patterns unsupportable by single current source multiplexed stimulation alone or summated in time for motor unit recruitment.

C. Electrode Waveforms

These electrodes generate excitatory contact waveforms and complementary contact waveforms to stimulate targeted nerves or nerve fibers. Stimulation frequency is adjustable from approximately 1 Hertz (Hz) to approximately 100 Hz or higher. Typical frequencies for producing a tetanic contraction range from approximately 15 Hz to approximately 60 Hz. Lowering the frequency to the lowest required for a smooth, tetanic, and comfortable contraction reduces device power consumption and reduces muscle fatigue elicited by electrical stimulation. These stimulation patterns are exemplary only, and not limited to what is described. While only excitatory contact waveforms and complementary contact waveforms are explained below, other stimulation waveforms of other stimulation frequencies may be used without departing from the scope of the invention.

1. Excitatory Contact Waveforms

Excitatory electrode contact waveforms may be symmetrical or asymmetrical biphasic, cathodic phase first, followed by a short interphase interval, followed by an anodic (charge recovery) phase. The first cathodic phase ranges from approximately 10 to approximately 1000 microseconds long. The interphase interval can be as short as approximately 10 microseconds and as long as approximately 250 microseconds, and is set to 50 microseconds by default. The interphase interval is set to be long enough to allow the first cathodic phase to achieve its full recruitment function before the charge recovery phase occurs. Shortening the interphase interval to less than the recruitment time would diminish the effect of the cathodic phase and waste a portion of the energy supplied during recruitment. The anodic phase duration and amplitude are approximately identical to the cathodic phase for a symmetrical biphasic waveform, and the anodic phase of an asymmetrical waveform is approximately six times the duration of the cathodic phase in certain embodiments, with a concomitant phase amplitude approximately one-sixth the amplitude of the cathodic phase.

In the symmetrical and asymmetrical waveforms, the charge delivered during the cathodic phase is approximately equal to the charge recovered in the anodic phase. In certain embodiments, ceramic coupling capacitors in series with the output circuitry to each electrode contact help maintain the charge balance and prevent the passage of direct current, known to be harmful to tissue and which may increase the likelihood of failure in feedthroughs of the electronics enclosure. The coupling capacitors must be large enough to pass current phases without significant droop.

2. Complementary Contact Waveforms

Complementary electrode contact waveforms have the opposite polarity as excitatory electrode contact waveforms, but similar amplitude and phase duration characteristics. If the waveform is symmetrical biphasic, the third phase of the waveform at the complementary contact is cathodic, and could excite nerves in its vicinity. If the waveform is asymmetrical, the third phase of the waveform would be cathodic as well, but its amplitude would be roughly one sixth of the excitatory contact amplitude, and would be unlikely to excite any nerves.

D. Electrode Power

In the embodiments discussed above, independent current sources power each electrode contact. Each contact is driven by its own current generator, which sources or sinks up to approximately 12.7 mA in 0.1 mA steps. The compliance voltage is the voltage that the current generator utilizes for constant current generation for each current source, and in the exemplary embodiment shown is approximately 18 volts. In other embodiments, compliance voltage ranges from approximately 15 to approximately 20 volts. The expected bipolar electrode to tissue impedance is approximately 500 to 1500 ohms. Assuming an electrode-to-tissue impedance of 1000 ohms, it would take roughly 1 volt of compliance voltage to drive 1 mA of current through the electrode contact, and roughly 12.7 volts to drive 12.7 mA of current through the electrode contact for the initial access voltage portion of the pulse, and higher voltages as the current is maintained through the coupling capacitor. Since the outputs are capacitively coupled, the compliance voltage should be greater than this initial access voltage to maintain the current for the duration of the pulse phase. Compliance voltage is chosen based on factors such as maximum current desired, maximum phase duration desired, coupling capacitor size, and expense of providing high voltage power supplies to maintain constant current for the duration of the pulse phase.

Total current delivered to all contacts typically does not exceed the steady state output of the IPG power supply. Current in this exemplary embodiment is limited to approximately a 20 mA concurrent output. Overall current consumption depends on many factors, including, for example, phase duration, phase amplitude, and pulse frequency. Taking these factors into account, the total current output in the exemplary embodiment is approximately 2 mA. The current and voltage levels in these embodiments are exemplary only however. Other power levels may be used without departing from the scope of the invention.

III. IPG Nerve Stimulation

The embodiments described above allow for accurate, selective nerve stimulation, including for example, the HGN. By accurately and selectively stimulating the HGN with multiple independent current sources and site-specific multiple contact electrodes, often in combination with patient specific stimulus programming, only the portions of the HGN responsible for non-timing dependent activation are recruited and activated, enabling accurate open-loop stimulation. These exemplary embodiments incorporate independent and concurrent stimulation, enabling optimal selective stimulation of only the desired portions of the HGN.

This independent and concurrent stimulation produces the desired tongue movement without needing to sense breathing related events to achieve desired results. Other embodiments of the IPG can include timed stimulation. Timed stimulation allows for triggered open loop or fully closed loop stimulation. Various examples of stimulation are discussed in U.S. Patent Application Nos. 60/978,519 and 61/017,614 filed on Oct. 9, 2007 and Dec. 29, 2007 respectively, which are incorporated herein by reference. The sections below describe how nerves are recruited, and include examples of stimulation patterns generated with these exemplary embodiments. These patterns are exemplary only, and not limited to those discussed below.

A. Nerve Structure, Activation, and Recruitment

One of the contributors to nerve activation threshold is nerve fiber diameter. Due to the electrical cable properties of the nerve fibers, large diameter nerve fibers have a lower excitation threshold than smaller diameter fibers, and are more easily excited by electrical stimulation. Thus, nerve fibers are more likely to be recruited by an electrical stimulation pulse if they are closer to the activating electrode, and/or have a larger diameter than other fibers.

B. Force Vectoring and Field Steering

Multiple contact electrodes may be used in conjunction with multiplexed stimulator systems to co-activate multiple muscle groups to achieve a desired muscle response. In activating the muscles of the tongue, hand, or forearm, for instance, several contacts may be sequentially energized to deliver interlaced pulses to first one contact and then another, to activate two or more muscle groups that when added result in a force vector in the desired direction. This is force vectoring.

Figure 10A:
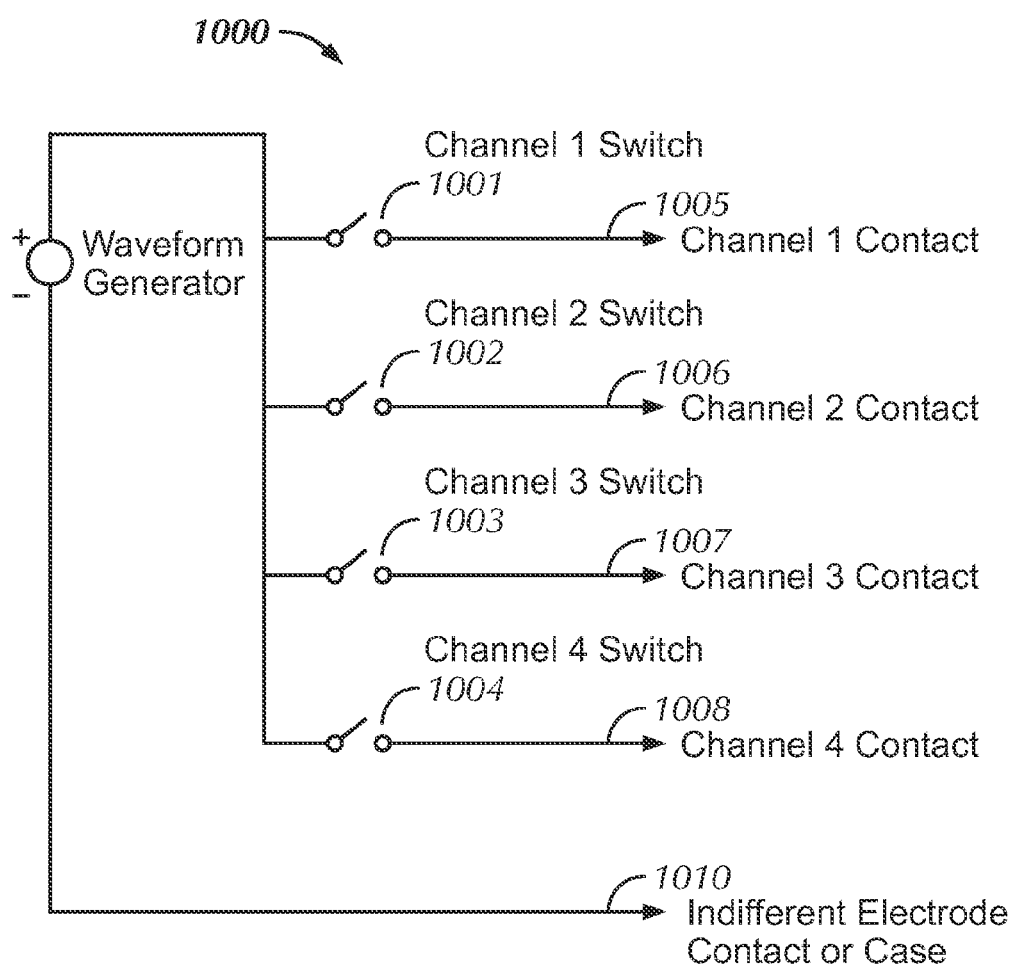
FIGS. 10A and 10B show an example of a multiplexed system using force vectoring.
Figure 10B:
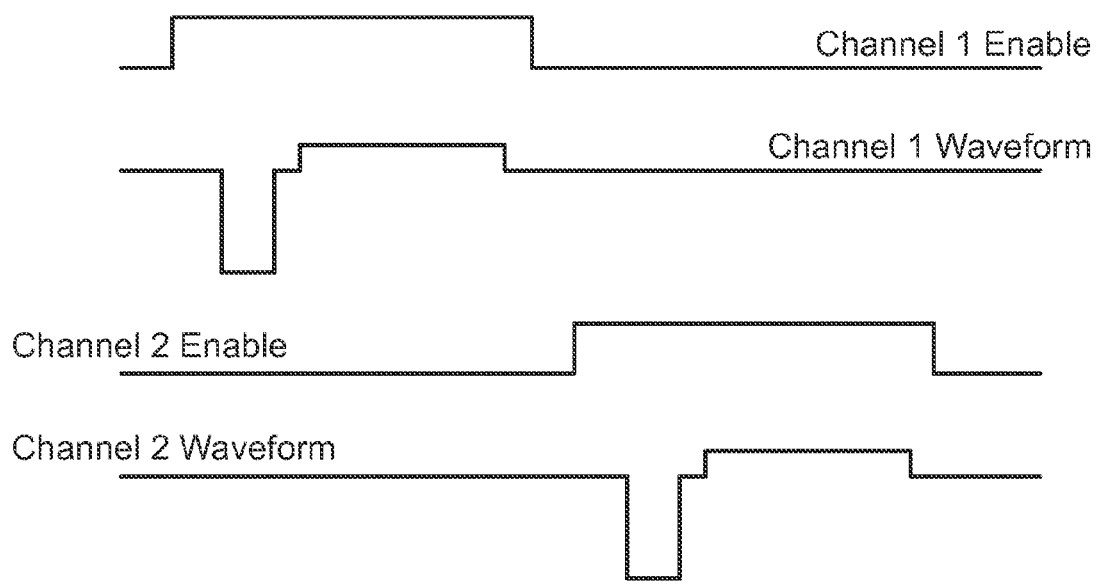

FIGS. 10A and 10B show an example of a multiplexed system using force vectoring. Even using force vectoring, multiplexed or single-source electrodes have limitations in the stimulation patterns they could deliver. For example, with a single cathodic phase current from a single contact, the nerve fibers closest to the contact are the first to be recruited or activated (assuming uniform distribution of fiber diameters, etc). As shown in FIG. 10A, even if the source were multiplexed to multiple contacts however, the waveform generator 1000 would connect to each contact 1005-1008 via a switching network 1001-1004. FIG. 10B illustrates this with an example. As shown in FIG. 10B, only a single waveform can be sent at any given time. First, channel 1 is enabled (i.e., switched on) and a waveform is generated for channel 1 by a single waveform source. When the channel 1 waveform is complete, channel 1 is disabled (i.e., switched off). Once channel 1 is disabled, channel 2 is enabled, and a waveform is generated for channel 2 using the same waveform source. Simultaneous transmission of multiple waveforms is not possible with this design.

Figure 11A:
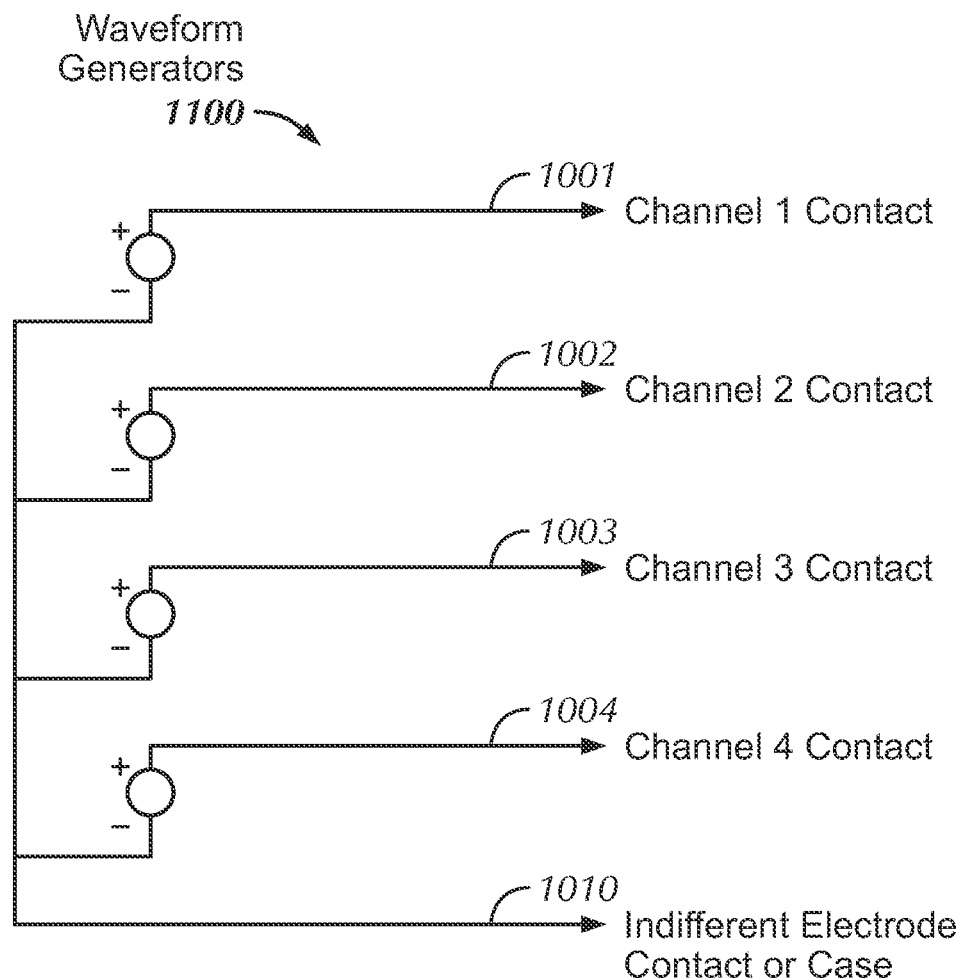
FIGS. 11A and 11B show exemplary embodiments of non-multiplexed waveform generators.
Figure 11B:
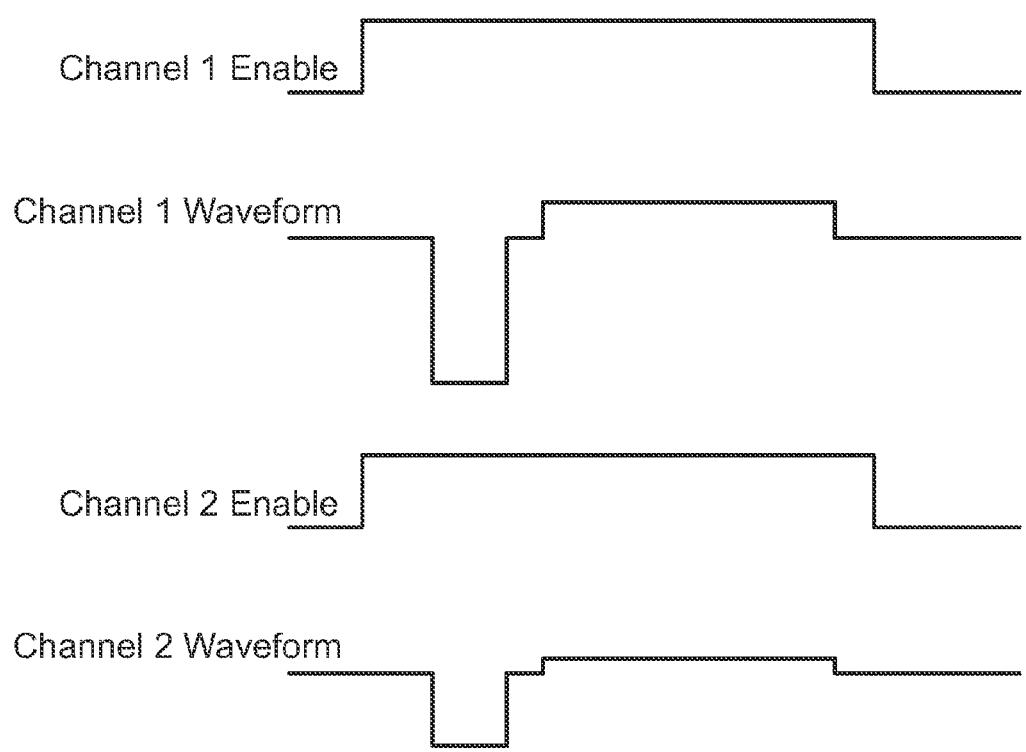

FIGS. 11A and 11B show exemplary embodiments of non-multiplexed waveform generators 1100. These embodiments are used for field steering. Field steering solves the limitations of force vectoring. Field steering uses independent current sources and multiple electrode contacts together to define a volume of activated nerve fibers. Field steering uses multiple independent current sources to generate highly selective patient-specific activating current volumes.

Field steering is more selective than simple force vectoring. Field steering (also known as current steering) enables activation of a particular region or volume of nerve fibers near two or more electrode contacts by controlling the cathodic phase amplitude generated by each of the contacts independently. For example, using two cathodic contacts 1101 and 1102 with equal phase amplitudes (for example by connecting two contacts to a single current source or by setting independent current sources to the same amplitude), applying a stimulus to the contacts defines a neural activation volume constrained to a region approximately equidistant between the two contacts. In this configuration, a sub-threshold phase current on each of the contacts 1101 and 1102 could be delivered, which combine to form an overlapping current field with supra-threshold current field. As previously discussed, with two electrodes of equal current the central volume between the electrodes is the activated nerve region.

Field steering allows the ability to change the activation area by changing the proportion of cathodic phase current from a 50-50 split (requiring independent multiple current sources), thereby shifting the current volume from the midline to a region closer to the higher phase current source electrode contact. In field steering, independent current sources are connected to individual electrodes and energized approximately simultaneously to define a volume where nerve fibers will be activated. In order to activate a selected pool of neurons located somewhere between two contacts, a stimulator delivers coincident stimulation pulses. They are delivered simultaneously rather than sequentially multiplexed. In the example shown in FIG. 11A, sub-threshold currents are delivered to each contact 1101-1104 so that the fields around the individual contacts are below the recruitment threshold. As shown in FIG. 11B, the currents need not be identical. The pulse phase durations are approximately equal, but amplitudes may differ because they are generated by independent current sources. The fields combine in the targeted nerve area to create pulses sufficient to stimulate the targeted nerve or nerves. Thus, nerve populations other than those lying directly under a stimulation electrode contact can be preferentially and selectively activated to achieve a desired stimulus pattern. This is important because the desired region of activation might not be positioned directly under a stimulation contact due to the surgical approach or a lack of a priori understanding of nerve fiber organization prior to the application of stimulation, but which allows for the later adjustment of this stimulation field to achieve the desired result.

IV. Stimulation Triggering and Measurement

The apparatus, system, and methods described above may use open loop stimulation, triggered open loop stimulation, and closed loop stimulation, either separately or in combination, to control stimulation. Closed loop can use sensors and signals to initiate stimulation and to regulate its output so that a desired output function is obtained. Triggered open loop stimulation uses one or more measurements as triggers for initiating stimulation. These triggers may be obtained using one or more internal sensors, external sensors, or a combination of both. Internal sensors can be included in the IPG implant, while external sensors would transmit trigger information to the IPG implant. The triggers can be transmitted to the IPG implant wirelessly (for example by RF, Bluetooth, or other wireless means known to those skilled in the art), or by operatively connecting the external sensor to the IPG implant.

Examples of triggers include, but are not limited to, snoring, airflow, actigraphy, hypoxia, tongue position, and tongue protrusion. In certain exemplary embodiments, snoring could be detected internally using a vibration sensor in the IPG implant. In other embodiments, snoring could be detected internally using an acoustic sensor and sound processor. In still other embodiments, snoring could be detected externally using, for example, a nasal canula or a microphone placed in the ear. Airflow could be measured externally using a nasal canula or thermistor and used as a trigger or as a closed loop feedback signal. Actigraphy could be measured using, for example, an accelerometer, which could be located internally or externally. Hypoxia could be measured internally using, for example, an infrared source and sensor in the IPG implant, or externally using an earlobe-monitoring unit. Tongue position could also be used as a trigger using, for example, a proximity sensor, while tongue protrusion could be used as a trigger using, for example, an accelerometer. These triggers could be used at any time, including initial placement, programming, and/or IPG implant calibration.

V. Auto Titration

Any combination of parameters measured in open loop, triggered open loop, and closed loop stimulation can be used to program and/or control stimulation. In certain embodiments, one or more measured parameters are used to alter stimulation programming automatically in real time in response to changes in user condition. This is auto titration.

Auto titration may be performed during initial implantation and programming, during normal IPG system operation, or both. For example, auto titration may be used to optimize IPG implant settings while the patient is in a medical facility, such as a clinic or hospital, a physician's office, a sleep laboratory, or while the patient is at home (home titration). Small changes to stimulation parameters and configurations are made while observing their effect on one or more indicators such as airway diameter, airway resistance, airflow, snoring, or other generally accepted measurements used to evaluate obstructive sleep apnea.

Clinician input and other related events may also be entered to associate these indicators with patient sleep phases, including EEG and manual selection/confirmation of phase identification. Since sleep phases greatly affect the range of sleep disordered breathing (SDB) measurements, and since there may be significant delays in effects resulting from changes in stimulation parameter and configuration changes, computers may be used to assist with data analysis and confirmation of clinician assessments in a semi-automated system. In certain titration embodiments, the titration system has an automated programming capability (i.e., an auto titration system). For example, certain exemplary titration embodiments use predetermined algorithms to alter stimulus in response to detection of apnea indicators. In certain exemplary embodiments, the auto titration system is portable.

Auto titration may also be used during normal IPG implant operation. For example, in certain embodiments a sensor, which may be in the IPG implant or the external patient controller, monitors a respiration indicator like air flow, for example. When the indicator drops, for example if flow decreases by 10% below average unobstructed sleeping patient flow, or snoring is detected, the IPG implant or external controller slowly increases stimulus to cause an improvement in the monitored indicator (e.g., an increase in airflow and/or a decrease in snoring). If the sensor is connected to the IPG implant, the IPG implant changes stimulation parameters. If the sensor is connected to an external controller, the controller changes simulation parameters, or it triggers a preprogrammed increase in the IPG implant. The indicators are exemplary only. Other indicators known to those skilled in the art may be used without departing from the scope of the invention.

It will be apparent to those skilled in the art that various modifications and variations can be made in the Apparatus, System, and Method for Selective Stimulation without departing form the spirit or scope of the invention. Thus, it is intended that the present invention cover the modifications and variations of this invention provided they come within the scope of the appended claims and their equivalents.

What is claimed is:

1. A method of treating sleep apnea using neurostimulation to control the position of a patient's tongue, comprising the steps of:
   implanting an electrode having a plurality of contacts into the patient to electrically couple the plurality of contacts to a Hypoglossal nerve of the patient;
   implanting an implantable pulse generator (IPG) into the sub-mandibular space of the patient, the IPG being electronically coupled to the electrode, the IPG comprising a symmetrical, chevron-shaped molded body having an apex at a distal end of the IPG, a coil at the apex of the chevron-shaped molded body, and an electronics enclosure at least partially integral with the chevron-shaped molded body and proximal to the coil, a first lead extending from the electronics enclosure and along a first leg of the chevron-shaped molded body, and a second lead extending from the electronics enclosure and along a second leg of the chevron-shaped molded body, the first leg extending proximally and laterally from a first side of the electronics enclosure, and the second leg extending proximally and laterally from a second side of the electronics enclosure opposite the first side of the electronics enclosure; and
   programming the IPG to deliver at least two electric signals to the plurality of contacts during a therapy session without taking into account a timing of respiration.

2. The method of claim 1 further comprising the step of: defining a neural activation volume by applying the at least two electric signals.

3. The method of claim 2, wherein the at least two electric signals are applied approximately simultaneously.

4. The method of claim 2, wherein at least one of the at least two electric signals is an asymmetric pulse.

5. The method of claim 1, wherein each of the at least two electric signals is a pulse train having a frequency between approximately 1 and approximately 100 Hertz.

6. The method of claim 1, wherein the electrode includes a cuff housing and wherein implanting the electrode includes wrapping the cuff housing around a portion of the Hypoglossal nerve.

7. The method of claim 6, wherein implanting the electrode includes wrapping the cuff housing around the portion of the Hypoglossal nerve at least once.

8. The method of claim 1, wherein the at least two electric signals are applied to the Hypoglossal nerve via an open loop system.

9. The method of claim 1, wherein the at least two electric signals are applied to a portion of the Hypoglossal nerve to stimulate at least two muscles of the tongue such that the stimulation of one of the at least two muscles of the tongue partially overlaps with the stimulation of another of the at least two muscles of the tongue.

10. The method of claim 1, wherein implanting an electrode having a plurality of contacts includes implanting a first electrode having at least one contact and implanting a second electrode having at least one contact.

11. The method of claim 1, further comprising the step of:
    applying the at least two electric signals via the plurality of contacts to a portion of the Hypoglossal nerve to stimulate at least two muscles of the tongue to prevent the tongue from blocking an airway during the therapy session,
    wherein applying the at least two electric signals includes driving each of the plurality of contacts by their own independent current source.

12. The method of claim 1, wherein the IPG further comprises:
    one or more holes extending through the chevron-shaped molded body along each side of the apex, each of the one or more holes having a complete perimeter defined by the IPG.

13. The method of claim 1, wherein the IPG is configured to be able to stimulate a left side Hypoglossal nerve, a right side Hypoglossal nerve, or both the left side and the right side Hypoglossal nerve, regardless of an orientation of the IPG as implanted.

14. The method of claim 1, wherein the IPG includes a first electrode lead coupled to the first lead and extending from the first leg of the chevron-shaped molded body, and a second electrode lead coupled to the second lead and extending from the second leg of the chevron-shaped molded body.

15. The method of claim 1, wherein closely tracing the entire outer perimeter of the chevron-shaped molded body of the IPG results in a chevron shape with smooth corners.

16. The method of claim 1, wherein implanting the IPG into the sub-manibular space of the patient includes selecting the IPG to be implanted independent of whether the electrode is implanted on the right and/or left side of the patient.

17. The method of claim 1, wherein the electrode is a first electrode having at least one first contact electrically coupled to a first Hypoglossal nerve of the patient, the method further comprising the steps of:
    implanting a second electrode having at least one second contact into a patient to electrically couple the at least one second contact to a second Hypoglossal nerve of the patient; and
    applying at least one of the at least two electric signals via the at least one first contact and at least one of the at least two electric signals via the at least one second contact to the first and second Hypoglossal nerves respectively to stimulate a portion of the first Hypoglossal nerve and a portion of the second Hypoglossal nerve to treat sleep apnea by preventing the tongue from blocking an airway during the therapy session.

18. The method of claim 1, wherein the first lead extends from the first side of the electronics enclosure and the second lead extends from the second side of the electronics enclosure.

* * * * *